United States Patent
Park et al.

(10) Patent No.: US 12,427,189 B2
(45) Date of Patent: *Sep. 30, 2025

(54) VACCINE COMPRISING EPITOPE OF HEAT SHOCK PROTEIN, AND USE THEREOF

(71) Applicant: ASTON SCI. CO., LTD., Seoul (KR)

(72) Inventors: Kyong Hwa Park, Seoul (KR); Jinho Kang, Seoul (KR)

(73) Assignee: ASTON SCI. CO., LTD., Seoul (KR)

( * ) Notice: Subject to any disclaimer, the term of this patent is extended or adjusted under 35 U.S.C. 154(b) by 377 days.

This patent is subject to a terminal disclaimer.

(21) Appl. No.: 17/885,255

(22) Filed: Aug. 10, 2022

(65) Prior Publication Data

US 2023/0084183 A1    Mar. 16, 2023

Related U.S. Application Data

(63) Continuation of application No. 16/997,307, filed on Aug. 19, 2020, now Pat. No. 11,446,368, and a continuation-in-part of application No. PCT/KR2019/001898, filed on Feb. 19, 2019.

(30) Foreign Application Priority Data

Feb. 19, 2018 (KR) ........................ 10-2018-0019123
Feb. 15, 2019 (KR) ........................ 10-2019-0018119

(51) Int. Cl.
| | | |
|---|---|---|
| *A61K 39/00* | (2006.01) | |
| *C07K 16/18* | (2006.01) | |
| *G01N 33/574* | (2006.01) | |
| *A61K 39/39* | (2006.01) | |
| *A61K 45/06* | (2006.01) | |

(52) U.S. Cl.
CPC ...... *A61K 39/001176* (2018.08); *A61K 39/00* (2013.01); *C07K 16/18* (2013.01); *G01N 33/57484* (2013.01); *A61K 39/39* (2013.01); *A61K 45/06* (2013.01); *C07K 2317/33* (2013.01)

(58) Field of Classification Search
CPC ... A61K 39/00; C07K 16/18; G01N 33/57484
See application file for complete search history.

(56) References Cited

FOREIGN PATENT DOCUMENTS

| | | |
|---|---|---|
| JP | 2003-533445 A | 11/2003 |
| JP | 5042301 B2 | 10/2012 |
| KR | 10-2007-0050918 A | 5/2007 |
| KR | 10-1594403 B1 | 2/2016 |
| WO | 2012/000443 A1 | 1/2012 |
| WO | 2013/134116 A1 | 9/2013 |

OTHER PUBLICATIONS

International search report for PCT/KR2019/001898 dated May 30, 2019.
Jinho Kang, "Development of Peptide Vaccine Targeting Heat Shock Protein 90 to Overcome Resistance to HER2-Targetd Drug in Breast Cancer", Thesis for the Degree of Doctor of Philosophy, Department of Medical Science Graduate School of Medicine Korea University, Aug. 2020.
Eun Joo Chung et al., "Heat shock proteins 70 and 90 from Clonorchis sinensis induce Th1 response and stimulate antibody production", Parasites & Vectors, 2017, vol. 10, No. 118, pp. 1-13 (13 pages).
R. Beck et al., "Molecular Chaperone Hsp90 as a Target for Oxidant-Based Anticancer Therapies", Current Medicinal Chemistry, 2011, vol. 18, No. 18, pp. 2816-2825 (10 pages).
Anne-Laure Joly et al., "Dual Role of Heat Shock Proteins as Regulators of Apoptosis and Innate Immunity", J Innate Immun, 2010, vol. 2, pp. 238-247 (10 pages).
Weilin Chen et al., "Efficient induction of antitumor T cell immunity by exosomes derived from heat-shocked lymphoma cells", Eur. J. Immunol., 2006, vol. 36, pp. 1598-1607 (10 pages).
Allegra et al., Vaccination of Multiple Myeloma: Current strategies and future prospects, Critical Reviews in Oncology/Hematology, 2015, 96, pp. 339-354 (Year: 2015).

*Primary Examiner* — Nelson B Moseley, II
*Assistant Examiner* — Dennis J Sullivan
(74) *Attorney, Agent, or Firm* — Sughrue Mion, PLLC

(57) ABSTRACT

A vaccine containing an epitope of a heat shock protein 90 and uses thereof are disclosed. The epitope(s) of heat shock protein 90 has the amino acid sequence of SEQ ID NO: 1 and/or 2. A multi-epitope vaccine containing the epitope(s) and a method for treating or preventing cancer using the same are disclosed.

13 Claims, 23 Drawing Sheets
(8 of 23 Drawing Sheet(s) Filed in Color)
Specification includes a Sequence Listing.

FIG. 2

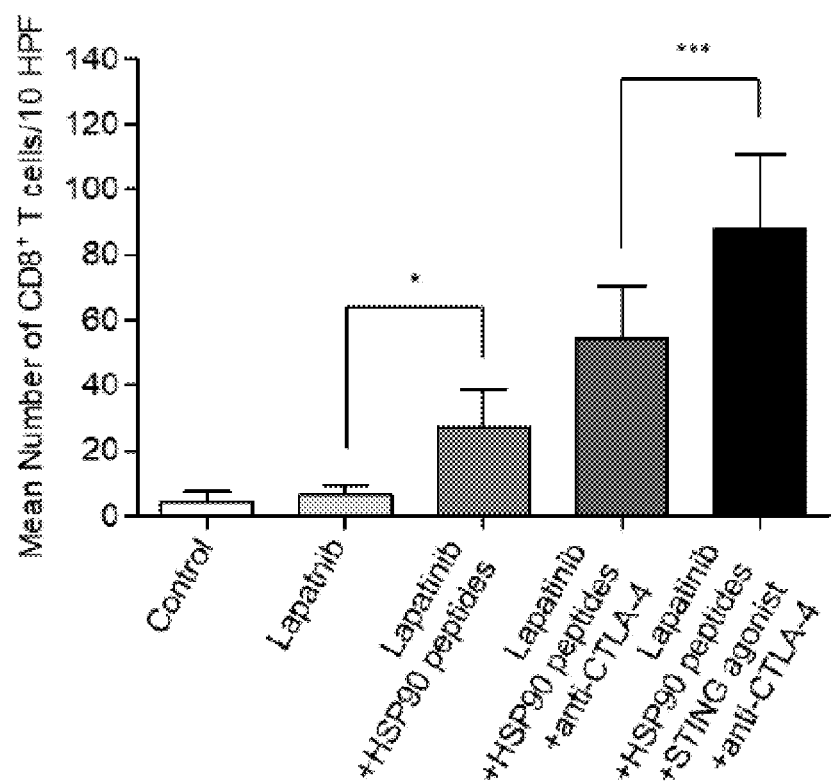

SEQUENCE LISTING

```
Sequence total quantity: 14
SEQ ID NO: 1            moltype = AA  length = 15
FEATURE                 Location/Qualifiers
REGION                  1..15
                        note = HSP90 p485-499
source                  1..15
                        mol_type = protein
                        organism = synthetic construct
SEQUENCE: 1
LYVRRVFIMD NCEEL                                                     15

SEQ ID NO: 2            moltype = AA  length = 15
FEATURE                 Location/Qualifiers
REGION                  1..15
                        note = HSP90 p527-541
```

```
source              1..15
                    mol_type = protein
                    organism = synthetic construct
SEQUENCE: 2
QSKILKVIRK NLVKK                                                           15

SEQ ID NO: 3        moltype = DNA   length = 45
FEATURE             Location/Qualifiers
misc_feature        1..45
                    note = HSP90 p485-499
source              1..45
                    mol_type = other DNA
                    organism = synthetic construct
SEQUENCE: 3
ttgtatgtac gcagagtttt catcatggat aactgtgagg agcta                          45

SEQ ID NO: 4        moltype = DNA   length = 47
FEATURE             Location/Qualifiers
misc_feature        1..47
                    note = HSP90 p527-541
source              1..47
                    mol_type = other DNA
                    organism = synthetic construct
SEQUENCE: 4
caaagcaaaa ttttgaaagt tatcaggaag aatttggtca aaaaatg                        47

SEQ ID NO: 5        moltype = AA    length = 15
FEATURE             Location/Qualifiers
REGION              1..15
                    note = HSP90 p109-123
source              1..15
                    mol_type = protein
                    organism = synthetic construct
SEQUENCE: 5
LYKDLQPFIL LRLLM                                                           15

SEQ ID NO: 6        moltype = AA    length = 15
FEATURE             Location/Qualifiers
REGION              1..15
                    note = HSP90 p145-159
source              1..15
                    mol_type = protein
                    organism = synthetic construct
SEQUENCE: 6
QAEIAQLMSL IINTF                                                           15

SEQ ID NO: 7        moltype = AA    length = 15
FEATURE             Location/Qualifiers
REGION              1..15
                    note = HSP90 p160-174
source              1..15
                    mol_type = protein
                    organism = synthetic construct
SEQUENCE: 7
YSNKEIFLRE LISNS                                                           15

SEQ ID NO: 8        moltype = AA    length = 15
FEATURE             Location/Qualifiers
REGION              1..15
                    note = HSP90 p220-234
source              1..15
                    mol_type = protein
                    organism = synthetic construct
SEQUENCE: 8
MTKADLINNL GTIAK                                                           15

SEQ ID NO: 9        moltype = AA    length = 15
FEATURE             Location/Qualifiers
REGION              1..15
                    note = HSP90 p255-269
source              1..15
                    mol_type = protein
                    organism = synthetic construct
SEQUENCE: 9
QFGVGFYSAY LVAEK                                                           15

SEQ ID NO: 10       moltype = AA    length = 15
FEATURE             Location/Qualifiers
REGION              1..15
```

```
                        note = HSP90 p296-310
source                  1..15
                        mol_type = protein
                        organism = synthetic construct
SEQUENCE: 10
TDTGEPMGRG TKVIL                                                      15

SEQ ID NO: 11           moltype = AA  length = 15
FEATURE                 Location/Qualifiers
REGION                  1..15
                        note = HSP90 p328-342
source                  1..15
                        mol_type = protein
                        organism = synthetic construct
SEQUENCE: 11
IVKKHSQFIG YPITL                                                      15

SEQ ID NO: 12           moltype = AA  length = 15
FEATURE                 Location/Qualifiers
REGION                  1..15
                        note = HSP90 p457-471
source                  1..15
                        mol_type = protein
                        organism = synthetic construct
SEQUENCE: 12
LEFRALLFVP RRAPF                                                      15

SEQ ID NO: 13           moltype = AA  length = 15
FEATURE                 Location/Qualifiers
REGION                  1..15
                        note = HSP90 p582-596
source                  1..15
                        mol_type = protein
                        organism = synthetic construct
SEQUENCE: 13
SELLRYYTSA SGDEM                                                      15

SEQ ID NO: 14           moltype = AA  length = 15
FEATURE                 Location/Qualifiers
REGION                  1..15
                        note = HSP90 p780-794
source                  1..15
                        mol_type = protein
                        organism = synthetic construct
SEQUENCE: 14
SVKDLVILLY ETALL                                                      15
```

VACCINE COMPRISING EPITOPE OF HEAT SHOCK PROTEIN, AND USE THEREOF

CROSS REFERENCE TO RELATED APPLICATIONS

This application is a continuation of U.S. application Ser. No. 16/997,307 filed Aug. 19, 2020, which is a continuation-in-part application of PCT/KR2019/001898 filed Feb. 18, 2019, which claims priority based on Korean Patent Application Nos. 10-2018-0019123 filed Feb. 19, 2018 and 10-2019-0018119 filed Feb. 15, 2019, of which the contents are incorporated in their entireties by reference.

SEQUENCE LISTING

The content of the electronically submitted sequence listing, file name: Sequence_Listing_As_Filed.xml; size: 18,584 bytes; and date of creation: Aug. 9, 2022, filed herewith, is incorporated herein by reference in its entirety.

FIELD OF THE INVENTION

The present invention relates to a vaccine comprising an epitope of a heat shock protein 90 and a combination therapy thereof. In more detail, it relates to an epitope(s) of heat shock protein 90 represented by the amino acid sequence of SEQ ID NO: 1 and/or 2, a multi-epitope vaccine comprising the same, and a method for treating or preventing cancer using the same.

BACKGROUND OF THE INVENTION

Immune response means antigenic challenge leads to activation of either B-lymphocytes or T-lymphocytes. These foreign substances may be immunogenic when they are able to produce specific immune response. They will stimulate immune cells and then give rise to immunological reaction (Humoral or cellular). Antigenic substances cannot yield directly immune response but need some help by some proteins (carrier proteins) and then they can react with antibodies. All immunogens are antigenic but not all antigens are immunogenic.

Foreignness is the most important factor that the substances should be recognized by the immune systems as foreign (non-self). The immune system develops a tolerance to the self-antigens.

The cell membrane consists of protein, phospholipids, cholesterol, and a trace of carbohydrate which are in the form of glycoproteins and glycolipids, where there are certain areas which are antigenic determinants called epitopes. The bacterial capsule is also immunogenic while bacteria without capsule have the surface structure which is immunogenic.

Antigens or immunogens are either proteins or large polysaccharides molecules and rarely if ever lipids. These are cell surfaces or membrane-bound antigens.

Proteins are very strong antigens. These are strong antigens because of their high molecular weight and structural complexity.

The higher the molecular weight, the better the molecule will act as an antigen. The number of epitopes is directly proportional to the size of the antigen.

Haptens are partial antigens. These are not immunogenic. Mostly too small to be immunogenic. Hapten needs carrier proteins like albumin, globulin and synthetic polypeptide to become immunogenic.

The larger molecules of antigens are more immunogenic because: (1) these are easily phagocytosed; (2) antibody formation is increased if the antigens are processed by antigen-presenting cells (APC); (3) the antigen which is difficult for phagocytosis is not immunogenic. If the molecular weight is >10,000 daltons, these are more immunogenic than the molecular weight of <10,000 daltons.

A neoantigenic determinant is an epitope on a neoantigen, which is a newly formed antigen that has not been previously recognized by the immune system. Neoantigens are often associated with tumor antigens and are found in oncogenic cells. Neoantigens and, by extension, neoantigenic determinants can be formed when a protein undergoes further modification within a biochemical pathway such as glycosylation, phosphorylation or proteolysis. This, by altering the structure of the protein, can produce new epitopes that are called neoantigenic determinants as they give rise to new antigenic determinants. Recognition requires separate, specific antibodies.

In modern times, many diseases have become readily treatable, and diseases that cannot be cured have almost disappeared. However, unlike other disease treatments, cancer is very difficult and requires complex treatment, and the complex treatments are also not completely effective. Recently, immunotherapy methods are emerging. Immunotherapy is a method of treating cancer by using the immune response in the patient's body. Cancer can be prevented through this immunotherapy method. According to the principle of a vaccine, cancer immunotherapy is a method of activating cancer-specific immune cells by administering an antigen that causes cancer, and then causing the activated immune cells to specifically attack cancer in the body. In addition, when a cancer-specific antigen is administered into the body without cancer, the immune cells that have not been activated are activated as cancer-specific memory immune cells, thereby specifically attacking the cancer cells in case of cancer.

Except for cancers caused by viruses, the numerous epitopes expressed by most cancer cells are actually expressed in normal cells rather than specific to cancer cells, but are more expressed in cancer cells.

Breast cancer is the second most common malignancy in women globally and the most common malignancy in East Asia. As of 2016, the incidence of breast cancer has more than doubled; the average age of domestic breast cancer patients is 51 years, which is about 15 years younger than that of the other countries. Overexpression of HER2 has been observed in approximately 25% of all breast cancers patients, and is associated with poorer overall survival and decreased time to relapse. HER2-positive breast cancer has a poor prognosis due to its aggressive biological properties and requires special care and treatment. In recently study, a successful targeted therapeutic strategy has been developed that the small molecule intracellular tyrosine kinase inhibitor, lapatinib (which targets simultaneously EGFR and HER2), and the monoclonal antibody, trastuzumab (which targets the extracellular domain of HER2) showed significant efficacy in HER2-positive breast cancer patients. The HER2 extracellular domain (ECD) and p95 have been reported to be expressed in some breast tumors. Some studies have reported a better response to lapatinib and trastuzumab for patients with HER2 amplified tumors who had higher expression of HER2 ECD. However, successful use of lapatinib and trastuzumab is also limited by various underlying mechanisms of therapeutic resistance. The mechanisms of resistance to HER2 target therapeutics include p95 HER2 receptors, disruption of receptor binding by MUC-1 glycoproteins, abnormal signaling pathways such as PTEN, and compensatory activation of other receptor signaling systems such as HER2/EGFR/IGF1R, but the mechanisms responsible for the resistance and therapies to overcome them are still not well elucidated.

Heat shock protein 90 (HSP90) is a type of chaperone whose main function is to restore the unstable conditions before freshly produced proteins have a normal structure. HSP90 safely guides the signaling molecules into the cytoplasm and nucleus in normal cells to complete the signal transduction process and regulate the activity of proteins involved in apoptosis, survival, and growth pathways. In addition, mutations in proteins that interfere with signal transduction, hypoxia, or poor nutrition can lead to changes in activity. Cancer cells with overexpression of unstable molecules because of gene amplifications or mutations evade cell death, which helps them to have functional intracellular signaling that can promote cell growth and survival. HSP90 client protein are proteins that regulate almost all biological processes in tumor growth, cell division, metastasis, and cell growth, such as EGFR, HER2, VEGFR, IGF1R, HIF-1α, MMP-2, MET, telomerase, Akt, Raf, CDK4 and Cyclin D.

Most of the important signal transduction pathway effectors implicated in anti-cancer resistance mechanism in breast cancer are the HSP90 client proteins. HSP90 is a chaperone for most of the important signal transduction pathway effector proteins involved in HER2-positive breast cancer, including HER2, ER, PR, and Akt, the downstream effector protein of PIC3K. In addition, higher expression of HSP90 is associated with poorer overall survival of breast cancer patients. Approximately 25% and 37% of breast and ovarian cancer patients, respectively, have demonstrated the expression of autoantibodies as an evidence of an autoimmune response to HSP90. In high-grade osteosarcoma patients, the expression of HSP90 autoantibody has been reported to correlate with tumor response after preoperative chemotherapy. Therefore, HSP90 is considered a potential new therapeutic target to improve treatment of HER2-positive resistant breast.

The HSP90 inhibitors including geldanamycin, 17-AAG, 17-DMAG, IPI-504, and SNX-5422 have been developed as ATPase domain targeted therapeutics. Phase I/II clinical trials are being conducted as single agent or in combination with other anticancer drugs. Tanespimycin has demonstrated efficacy in a Phase I/II clinical trial when combined with trastuzumab in patients with trastuzumab-resistant breast cancer, suggesting the possibility that HSP90 inhibitors may contribute to overcoming trastuzumab resistance. Despite of promising efficacy, further clinical development was halted because of frequently observed toxicities such as hepatotoxicity, anemia, diarrhea, and chest pain. Therefore, developments of safer HSP90 targeted therapeutics and identification of biomarkers for rational clinical application are required.

So far, cancer vaccines have been developed using multiple platforms, including the direct use of cancer cells, peptides, and DNA. In the early stages of the development of cell-based cancer vaccines, mixed inactivated cancer cells or cancer cell fusion agents with adjuvants were utilized, which were applied to genes encoding cytokines and costimulatory molecules. In vitro culturing of dendritic cells and cancer antigen has been attempted as cancer vaccine therapeutic to present antigens of cancer cells. Cancer vaccines have been developed as DNA vaccine, peptide vaccine and cell vaccine according to the type and delivery method of the antigen. In a recent study, HSPPC-96 was developed in an autologous tumor-derived gp96HSP peptide complex in a patient. The HSP complex induces an anti-cancer immune response by binding to the CD91 receptor of antigen-presenting cells. Despite being safe, being able to induce effective immune responses, and showing long-term immune memory, the use of HSPPC-96 has been limited in patients because of difficulty in tumor cell acquisition. In addition, HSP110-gp100 has been demonstrated to elicit an antigen-specific IFN-γ production and a cytotoxic t-cell response, but is still preclinical stage. Peptide vaccines are expected to be the most potent next-generation cancer vaccines, and many studies have been conducted in this regard.

In many studies, strategies for several effective therapeutic vaccines have emerged, and immunotherapy has been widely used as an important tool for the treatment of cancer patients. The therapeutic vaccine not only expands tumor-specific T cells from the naïve repertoire, but also reactivates existing tumor-specific T cells, requiring tumor-specific antigens and appropriate adjuvants for optimal T cell activation. Importantly, the use of the vaccine alone has a weak natural T cell immune response, and thus the efficacy of treatment should improve using immune checkpoint inhibitors and appropriate adjuvants.

Agonist ligands for the stimulator of interferon genes (STING) have shown that type-I interferon (IFN-I) plays an important role in both innate and adaptive anti-tumor immune responses, especially as vaccine adjuvants in cancer immunotherapy. In addition, STING has been shown to recruit TBK1 to activate IRF3, including IFN-I induction and production of specific chemokines. Recent advances in various cancer therapies are based on immune checkpoint blockade and STING agonists that utilize the basic ability of the immune system to generate innate and adaptive antitumor immunity by regulating the pathways associated with T cells and type I IFN, such as CTLA-4, PD-1, and DMXAA. Therefore, to improve the therapeutic effect, development of HSP90 targeted therapy is urgently required because the combination therapy with established anticancer agents, immune checkpoint blockade, and STING agonist can be efficacious.

BRIEF SUMMARY OF THE INVENTION

To overcome the limitations of existing HSP90 targeted therapeutics and improve the therapeutic effect of HER2 target-resistant breast cancer, the present inventors have developed the HSP90 target peptide vaccine and investigated the role and mechanism of vaccine treatment in HSP90 target-resistant breast cancer.

The first aspect of the present invention provides a multi-epitope vaccine(s) comprising an epitope represented by the amino acid sequence of SEQ ID NO: 1 and/or an epitope represented by the amino acid sequence of SEQ ID NO: 2.

Preferably, the multi-epitope vaccine could be a mixture of an epitope represented by the amino acid sequence of SEQ ID NO: 1 and/or an epitope represented by the amino acid sequence of SEQ ID NO: 2.

The multi-epitope vaccine of the present invention can induce the production of antibodies and/or activation of immune cells that recognize heat shock protein 90 as an antigen. In this case, the antibody and/or immune cell may target a target cell that expresses heat shock protein 90 on the cell membrane surface.

In addition, the multi-epitope vaccine of the present invention can be used to prevent or treat cancer.

For example, a multi-epitope vaccine can include a recombinant multi-epitope protein produced from a multi-epitope vaccine gene containing a nucleic acid encoding an epitope represented by the amino acid sequence of SEQ ID NO: 1 and/or a nucleic acid encoding an epitope represented by the amino acid sequence of SEQ ID NO: 2.

The second aspect of the present invention provides a multi-epitope vaccine gene comprising a nucleic acid encoding an epitope represented by the amino acid sequence of SEQ ID NO: 1 and/or a nucleic acid encoding an epitope represented by the amino acid sequence of SEQ ID NO: 2.

In this case, the nucleic acid may be in the form of a recombinant vector or an expression vector. On the other hand, the nucleic acid encoding the epitope represented by the amino acid sequence of SEQ ID NO: 1 may be represented by the nucleotide sequence of SEQ ID NO: 3, and the nucleic acid encoding the epitope represented by the amino acid sequence of SEQ ID NO: 2 may be represented by the nucleotide sequence of SEQ ID NO: 4.

The multi-epitope vaccine gene of the second aspect of the present invention may be one used to prepare the multi-epitope vaccine of the first aspect of the present invention in vivo or in vitro.

A third aspect of the present invention provides a vaccine composition comprising
(1) a multi-epitope vaccine comprising an epitope represented by the amino acid sequence of SEQ ID NO: 1 and/or an epitope represented by the amino acid sequence of SEQ ID NO: 2; or
(2) a multi-epitope vaccine gene comprising a nucleic acid encoding an epitope represented by the amino acid sequence of SEQ ID NO: 1 and/or a nucleic acid encoding an epitope represented by the amino acid sequence of SEQ ID NO: 2; and
an adjuvant.

A fourth aspect of the present invention provides a composition for preventing or treating cancer, comprising
(1) a multi-epitope vaccine comprising an epitope represented by the amino acid sequence of SEQ ID NO: 1 and/or an epitope represented by the amino acid sequence of SEQ ID NO: 2; or
(2) a multi-epitope vaccine gene comprising a nucleic acid encoding an epitope represented by the amino acid sequence of SEQ ID NO: 1 and/or a nucleic acid encoding an epitope represented by the amino acid sequence of SEQ ID NO: 2.

At this time, the composition for preventing or treating cancer further contains an immune checkpoint inhibitor against any one selected from the group consisting of CTLA-4 (cytotoxic T-lymphocyte-associated protein 4), PD-1 (Programmed cell death protein 1), LAG-3 (Lymphocyte Activation Gene-3), TIM-3 (T-cell Immunoglobulin and Mucin-domain containing-3), TIGIT (T-cell Immunoreceptor with IG and ITIM domain), and VISTA (V-domain Ig Suppressor of T cell Activation); and/or
STING (Stimulator of Interferon gene) agonist.

The fifth aspect of the present invention provides a multi-epitope vaccine-specific antibody, which is obtained from an animal inoculated with the multi-epitope vaccine of the first aspect of the present invention or the multi-epitope vaccine gene of the second aspect of the present invention.

In this case, the antibody may induce antibody-dependent cell-mediated cytotoxicity (ADCC) and/or complement-dependent cytotoxicity (CDC).

In addition, the antibody may target tumor cells.

A sixth aspect of the present invention provides a composition for preventing or treating cancer, comprising the multi-epitope vaccine-specific antibody of the fifth aspect of the present invention; and a use of the composition in preventing or treating cancer. Thus, the sixth aspect of the invention also encompass a method for preventing and/or treating a subject with cancer comprising administering to the subject a composition comprising the multi-epitope vaccine-specific antibody of the fifth aspect.

A seventh aspect of the present invention provides an antibody (Ab) or antibody fragment that specifically binds to the epitope represented by the amino acid sequence of SEQ ID NO: 1 or the epitope represented by the amino acid sequence of SEQ ID NO: 2.

The antibody (Ab) or antibody fragment may target heat shock protein 90 and/or tumor cells.

The eighth aspect of the present invention provides a composition or kit for detecting an immune cell and/or antibody targeting an antigen of a tumor cell, comprising an epitope represented by the amino acid sequence of SEQ ID NO: 1 and/or an epitope represented by the amino acid sequence of SEQ ID NO: 2; and a use of the composition or kit in detecting an immune cell and/or antibody targeting an antigen of a tumor cell. Thus, the eighth aspect of the invention also encompass a method for detecting an immune cell and/or antibody targeting an antigen of a tumor cell in a biological sample comprising contacting the composition with the biological sample and detecting the immune cell and/or antibody.

The ninth aspect of the present invention provides a method for producing an immune cell and/or antibody targeting an antigen of a tumor cell, comprising the step of boosting and/or separating immune cells and/or antibodies targeting tumor cells from the biological sample using an epitope represented by the amino acid sequence of SEQ ID NO: 1 and/or an epitope represented by the amino acid sequence of SEQ ID NO: 2.

The tenth aspect of the present invention provides composition or kit for monitoring immune response to an antigen of a tumor cell, comprising
the epitope represented by the amino acid sequence of SEQ ID NO: 1 and/or the epitope represented by the amino acid sequence of SEQ ID NO: 2, or
an antibody (Ab) or antibody fragment that binds to the epitope.

The epitope may bind to antibodies, B cells, and/or T cells, or the antibody (Ab) or antibody fragment may bind to tumor cells.

An eleventh aspect of the present invention provides a method for manufacturing an epitope or a peptide vaccine, comprising the step of:
selecting the amino acid sequence of SEQ ID NO: 1 and/or the amino acid sequence of SEQ ID NO: 2; and
using the amino acid sequence(s) selected in the previous step, to synthesize an epitope that boosts immune cells or induces antibodies targeting tumor cells or binds to immune cells or antibodies targeting tumor cells.

The epitope may bind to an antibody or may bind to a T cell receptor, a B cell receptor, and/or a major histocompatibility complex (MHC).

A twelfth aspect of the present invention provides a method for manufacturing an epitope or a peptide vaccine, comprising the step of:
designing an epitopes of heat shock protein 90 using a sequence selected from the group consisting of amino acid sequences of SEQ ID NOs: 1, 2, and 5 to 14; and
synthesizing the epitope that binds to MHC class II using the amino acid sequence(s) selected in the previous step.

The synthesized epitope can be used to prepare an antibody (Ab) or antibody fragment targeting heat shock protein 90 or tumor cells. In addition, the synthesized epitope can be used to prepare a vaccine targeting tumor cells.

The vaccine composition of the present invention containing the epitope of the heat shock protein 90 is universally usable in the majority of patients, is easy to industrialize, and has remarkably excellent antitumor effects, so it can be economically used to prevent and treat cancer. Further, development of peptide vaccine targeting Heat Shock Protein 90 of the present invention overcomes resistance to HER2-targeted drug.

BRIEF DESCRIPTION OF THE DRAWINGS/FIGURES

The patent or application file contains at least one drawing executed in color. Copies of this patent or patent application publication with color drawing(s) will be provided by the Office upon request and payment of the necessary fee.

FIG. 1. shows that HER2-positive breast cancer patients can have immunity to HSP90. HSP90-specific IgG immunity was examined by ELISA in 25 patients with HER2 positive breast cancer and 25 volunteer donors. Bold lines, mean level of HSP90-specific IgG immunity for each group. ***$p<0.0001$ in Student's t-test.

FIG. 2 is prediction and selection of possible MHC class II binding HSP90 peptide. Eleven peptides with highest binding affinity across multiple MHC class II alleles were selected. Colors represent final scores from 5 algorithms for each peptide sequences from dark red to light blue in the order of rank scores. Colors strata are as follows: dark red, >9,000; red, 8,000 to 9,000; orange, 7,000 to 8,000; light orange, 6,000 to 7,000; gold, 5,000 to 6,000; yellow, 4,000 to 5,000; light yellow, 3,000 to 4,000; light green, 2,000 to 3,000; light blue, 1,000 to 2,000.

FIG. 3 shows that human T cell responses specific for HSP90 peptides can be recognized. HSP90 peptides was profiled antigen-specific responses by IFN-γ and IL-10 ELISPOT assay in human PBMCs from 10 volunteer donors. White columns, IFN-γ; black columns, IL-10, columns, mean of relative spots to No Antigen wells for six replicates; bars, SD.

FIGS. 4A-4B are result that immunogenicity of multiple HSP90 peptides shows potent antigen-specific T cell responses in mouse model. Mice were either immunized s.c with 100 μg of each HSP90 peptides or PBS as a mixture in complete Freund's adjuvant (CFA)/incomplete Freund's adjuvant (IFA). Three immunizations were given 10 days apart. Ten days after the third vaccination, the spleen was harvested from mice. In FIG. 4A, immunogenicity of eleven HSP90 peptides was evaluated antigen-specific T cell responses by IFN-γ ELISPOT assay. In FIG. 4B, two selected of HSP90 peptides was evaluated antigen-specific T cell responses by IFN-γ ELISPOT assay in mice. No Antigen (No Ag) and tetanus toxoid (TT) peptide, negative control; concanavalin A, positive control. The error bars represent the standard deviation. $p<0.01$, *$p<0.001$ in one-way ANOVA.

FIGS. 5A-5D show that HSP90-specific immunity inhibits tumor growth in neu-transgenic mice. Mice were immunized s.c injection with HSP90 peptide 100 μg or PBS as a mixture in CFA/IFA. Three immunizations were given 10 day apart. 7 days after the third vaccination, neu-transgenic mice were implanted with $5 \times 10^5$ mouse mammary carcinoma (MMC) cells. 3 weeks after tumor implantation, spleen and tumor was harvested in mice. In FIG. 5A, images of the tumor, and the graph represent tumor volume in each group: control (PBS) and HSP90 peptides (p485 and p527). In FIG. 5B, two selected HSP90 peptides was evaluated HSP90-specific T cell responses by IFN-γ ELISPOT assay. In FIG. 5C, the expression level changes of HER2 ECD were evaluated by ELISA assay in serum of mice. In FIG. 5D, the expression level changes of HER2-related proteins were examined by western blot analysis from control and HSP90 peptides tumor. β-Actin was used as an internal control. The error bars represent the standard deviation. NS, not significant, *$p<0.05$, ***$p<0.001$ in Student's t-test.

FIGS. 6A-6B show that In vivo CD4+ or CD8+ T cell depletion and tumor growth inhibiting efficacy of HSP90 peptides. Mice were immunized i.p injection with 200 μg of anti-CD4 and/or anti-CD8 mAbs 3, 2, 1 days before and then HSP90 peptides immunized. Three immunizations were given 10 day apart. Ten days after the third vaccination, MMC cells ($5 \times 10^5$) were implanted s.c in mice. After the first immunization, anti-CD4 or anti-CD8 mAbs were i.p injected with 200 μg twice a week until the end of experiment. FIG. 6A is the graph representing tumor volume in each group: control (PBS+rat IgG), HSP90 peptides, HSP90 peptides+anti-CD4, HSP90 peptides+anti-CD8 and HSP90 peptides+anti-CD4+anti-CD8. The error bars represent the standard deviation. FIG. 6B shows representative staining results from hematoxylin and eosin (H&E) and immunohistochemical staining for CD4$^+$ and CD8$^+$ T cells in tumor tissues isolated from neu-transgenic mice. Clusters of CD4$^+$ and CD8$^+$ T cells are marked by box and arrow. Scale bar=100 μm. ***$p<0.001$ in two-way ANOVA.

FIGS. 7A-7F show that the combination effect of HSP90 peptides and STING agonist enhances HSP90-specific immunity in neu-transgenic mice. Mice (4 per group) were implanted s.c with $5 \times 10^5$ MMC cells. When the tumor reached a size greater than 100 mm$^3$, mice were immunized s.c injection with HSP90 peptide vaccine and/or i.p injection with STING agonist. Three immunizations were given 10 days apart. in FIG. 7A, the graph represents tumor volume in each group: control (PBS+DMSO), only HSP90 peptides, only STING agonist, and HSP90 peptides+STING agonist. In FIG. 7B, the expression level changes of HER2 ECD was evaluated by ELISA assay in serum of mice. In FIGS. 7C-7F, HSP90-specific T cell responses were evaluated by IFN-γ ELISPOT assay in splenocytes from all experiment group. The error bars represent the standard deviation. Columns, mean spots for six replicates; white column, No antigen; gray column, TT peptide; dark gray column, HSP90 peptides; black column, concanavalin A. *$p<0.05$, $p<0.01$, *$p<0.001$ in one-way ANOVA.

FIG. 8 shows that combination therapy with HSP90 peptides and STING agonist improves survival in neu-transgenic mice. Mice (6 per group) were implanted s.c with $5 \times 10^5$ MMC cells. When the tumor reached a size greater than 100 mm$^3$, the mice were immunized s.c injection with HSP90 peptide vaccine and/or i.p injection with STING agonist. Three immunizations were given 10 days apart. The survival rate was assessed up to 90 days in combination therapy with HSP90 peptides and STING agonist after tumor implantation. Kaplan-Meier survival curves of mice (6 per group) that were implanted with MMC cells and were treated with different the combinations of HSP90 peptides and STING agonist. ***$p<0.001$.

FIGS. 9A-9G show that the combination effect of HSP90 peptides/STING agonist/anti-CTLA-4 Ab inhibits tumor growth in neu-transgenic mice. Mice (4 per group) were implanted s.c with $5 \times 10^5$ MMC cells. When the tumor reached a size greater than 100 mm$^3$, the mice were immunized s.c injection with HSP90 peptides and/or i.p injection with STING agonist. Three immunizations were given 10 days apart. After the first immunization, anti-CTLA-4 Ab was injected i.p twice a week until the experiment end. In FIG. 9A, the graph represents tumor volume in each group: control (PBS+Hamster IgG+DMSO), HSP90 peptides, HSP90 peptides+anti-CTLA-4 Ab, STING agonist+anti-CTLA-4 Ab, and HSP90 peptides+STING agonist+anti-CTLA-4 Ab. In FIG. 9B, the expression level changes of HER2 ECD was evaluated by ELISA assay from serum of mice. In FIGS. 9C-9G, HSP90-specific T cell responses were assessed by IFN-γ ELISPOT using splenocytes from all experimental mice. The error bars represent the standard deviation. Columns, mean spots for six replicates; white column, No antigen; gray column, TT peptide; dark gray column, HSP90 peptides; black column, concanavalin A. ***$p<0.001$ in one-way ANOVA.

FIGS. 10A-10C show that combination therapy with HSP90 peptides/STING agonist/anti-CTLA-4 Ab enhances CD4+ and CD8+ T cells in tumor tissue. Mice (4 per group) were implanted s.c with $5\times10^5$ MMC cells. When the tumor reached a size greater than 100 mm$^3$, the mice were immunized s.c injection with HSP90 peptides and/or i.p injection with STING agonist. Three immunizations were given 10 days apart. After the first immunization, anti-CTLA-4 Ab was injected i.p twice a week until the experiment end. FIG. 10A shows representative staining results from hematoxylin and eosin (H&E) and immunohistochemical staining for CD4 and CD8 T cells in tumor tissues isolated from neu-transgenic mice. In FIG. 10B, the graph represent mean number of CD8$^+$ T cells per 10 high-power field (HPF) in tumor from each experiment mice. The error bars represent the standard deviation. In FIG. 10C, the expression level changes of HER2-related proteins were examined by western bolt analysis in control and experimental group tumors (representative 2 per group). β-actin was used as an internal control. Clusters of CD4 and CD8 T cells are marked by box and arrow. Scale bar=100 μm. NS, not significant; ***$p<0.001$ in one-way ANOVA.

FIGS. 11A-11B show establishment of lapatinib-resistant mouse mammary carcinoma (LR-MMC) cells and mouse model. MMC cells and lapatinib-resistant MMC cells $1\times10^6$ MMC cells and lapatinib-resistant MMC cells. When the tumor reached a size greater than 100 mm$^3$, the mice were administrated by 5 times weekly to orally gavage with lapatinib (75 mg/kg) until the experimental end. In FIG. 11A, the cell viability was evaluated after lapatinib treatment in a dose-dependent manner by the MTT assay from MMC and LR-MMC cells. In FIG. 11B, the graph represent tumor volume in each group: MMC (control and lapatinib; n=5) and LR-MMC (control and lapatinib; n=5). The error bars represent the standard deviation. NS, not significant. *$p<0.05$ versus MMC in one-way ANOVA.

FIGS. 12A-12B show that combination effect with HSP90 inhibitor (17-DMAG) and lapatinib diminishes the expression of HER2 related protein in LR-MMC cells. In FIG. 12A, the expression level changes of HER2-related and HSP90 proteins were examined by western bolt analysis in MMC and LR-MMC cells. In FIG. 12B, changes of the expression levels of HER2-related and HSP90 protein was evaluated by western blot analysis after combination treatment with lapatinib (30 nM) and/or 17-DMAG (10 nM) in MMC and LR-MMC cells. β-Actin was used as a loading control. MMC, mouse mammary carcinoma; LR-MMC, lapatinib-resistant MMC.

FIGS. 13A-13H show that combination effect with lapatinib/HSP90 peptides/STING agonist/anti-CTLA-4 Ab enhances antitumor activity and HSP90-specific immunity in lapatinib-resistance mouse model. Mice (4 per group) were implanted s.c with $1\times10^6$ LR-MMC cells. When the tumor reached a size greater than 100 mm$^3$, the mice were immunized s.c injection with HSP90 peptides and/or i.p injection with STING agonist. Three immunizations were given 7 days apart. After first immunization, anti-CTLA-4 Ab was injected i.p twice a week, and lapatinib was administrated by 5 times weekly to orally gavage until the experiment end. In FIG. 13A, the graph represent tumor volume in each group: control (PBS+Hamster IgG+DMSO), Lapatinib, Lapatinib+HSP90 peptides, Lapatinib+HSP90 peptides+anti-CTLA-4, and Lapatinib+HSP90 peptides+STING agonist+anti-CTLA-4. In FIGS. 13B-13F, HSP90-specific IFN-γ-secreting T cell response was evaluated by IFN-γ ELISPOT using splenocytes from all experimental mice. (G-H) The potential epitope-spreading responses of HER2, c-MET and HIF-1α peptide were assessed by ELISPOT assay using splenocytes from selected groups. The error bars represent the standard deviation. Columns, mean spots for six replicates; white column, No antigen; gray column, TT peptide; dark gray column, HSP90 peptides; black column, concanavalin A. *$p<0.05$, *$p<0.001$ in one and two-way ANOVA.

FIGS. 14A-14B show that combination therapy with lapatinib/HSP90 peptides/STING agonist/anti-CTLA-4 Ab enhances CD4+ and CD8+ T cells in tumor tissue. Mice (4 per group) were implanted s.c with $1\times10^6$ LR-MMC cells. When the tumor reached a size greater than 100 mm$^3$, the mice were immunized s.c injection with HSP90 peptides and/or i.p injection with STING agonist. Three immunizations were given 7 days apart. After the first immunization, anti-CTLA-4 Ab was injected i.p twice a week and lapatinib was administrated by 5 times weekly to orally gavage at until the experiment end. FIG. 14A shows representative staining results from hematoxylin and eosin (H&E) and immunohistochemical staining for CD4+ and CD8+ T cells in tumor tissues isolated from neu-transgenic mice. In FIG. 14B, the graph represents mean number of CD8+ T cells per 10 high-power field (HPF) in tumor from each experiment mice. The error bars represent the standard deviation. Clusters of CD4+ and CD8+ T cells are marked by box and arrow. Scale bar=100 μm. *$p<0.05$, ***$p<0.001$ in one-way ANOVA.

DETAILED DESCRIPTION OF THE INVENTION

Immune responses play a critical role in fighting tumors and viral infections. An antigenic epitope is a basic unit that elicits either a cellular or a humoral immune response. A multi-epitope vaccine composed of a series of or overlapping peptides is therefore an ideal approach for the prevention and treatment of tumors or viral infections.

Figure 15:
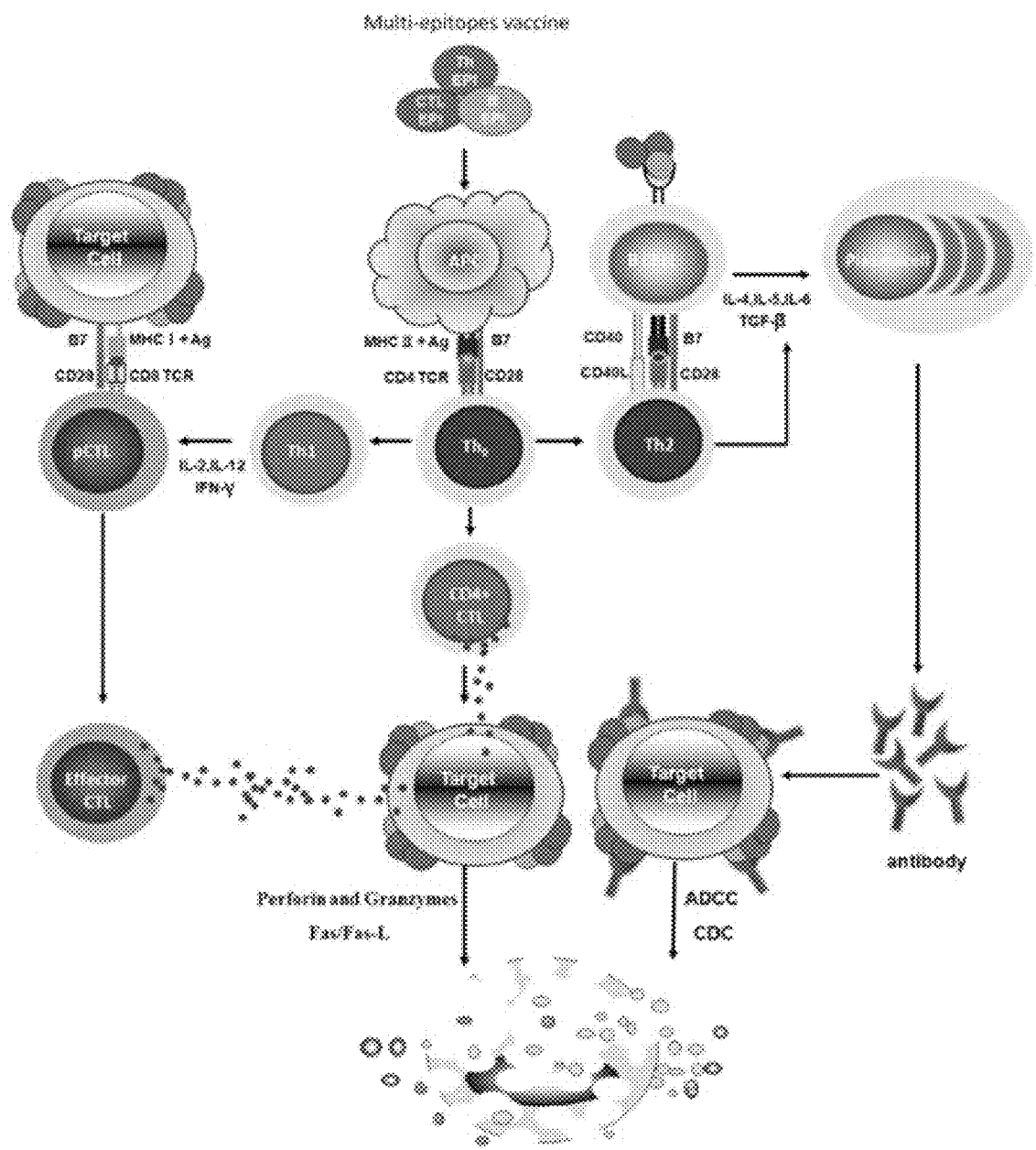
FIG. 15 shows the molecular and cellular mechanism of immune responses induced by a multi-epitope vaccine.

An ideal multi-epitope vaccine should be designed to include epitopes that can elicit CTL, Th and B cells and induce effective responses against a targeted tumor or virus (FIG. 15).

Multi-epitope vaccines can be composed of CTL, Th and B-cell epitopes in a series or overlapping epitope peptides. Through TCR, CD8$^+$ precursor CTL (CD8$^+$ pCTL) recognizes the complex of CTL antigen peptides bound to MHC class I molecules that are displayed by target cells (tumor cells or virus-infected cells). Antigen presenting cells (APC) take up the multi-epitope vaccine and present the Th antigen peptides bound to MHC class II molecules to Th0 cells. Th0 cells are differentiated into Th1, Th2 and CD4+ CTL cells. Th1 cells secrete cytokines that stimulate CD8+ pCTL to generate effector CTL cells, the latter of which will kill the target cells by both the perforin/granzyme and the Fas/FasL pathways. Th2 cells recognize the Th epitope bound to MHC class II molecules that are presented by B cells. After being activated, Th2 cells express CD40L molecules and secrete cytokines to stimulate B-cell activation; CD4+ CTL cells secrete cytotoxins, directly killing the target cells by releasing granules containing perforin and granzyme B. B cells recognize and take up the B epitopes of the multi-epitope vaccine by BCR, presenting the Th epitopes bound to MHC class II molecules to activate Th2 cells. The B cells then proliferate and differentiate into plasma cells after binding to the CD40L molecules and cytokines provided by activated Th2 cells. The plasma cells secrete multi-epitope vaccine-specific antibodies to perform anti-tumor or anti-virus tasks in target cells by antibody-dependent cell-mediated cytotoxicity (ADCC) and complement-dependent cytotoxicity (CDC).

Compared to classical vaccines and single-epitope vaccines, multi-epitope vaccines have unique design concepts with the following properties: (I) they consist of multiple MHC-restricted epitopes that can be recognized by TCRs of multiple clones from various T-cell subsets; (II) they consist of CTL, Th and B-cell epitopes that can induce strong cellular and humoral immune responses simultaneously; (III) they consist of multiple epitopes from different tumor or virus antigens that can expand the spectra of targeted tumors or viruses; (IV) they introduce some components with adjuvant capacity that can enhance the immunogenicity and long-lasting immune responses; and (V) they reduce unwanted components that can trigger either pathological immune responses or adverse effects. Well-designed multi-epitope vaccines with such advantages should become powerful prophylactic and therapeutic agents against tumors and viral infections.

Current problems in the field of multi-epitope vaccine design and development include the selection of appropriate candidate antigens and their immunodominant epitopes and the development of an effective delivery system. Development of a successful multi-epitope vaccine first depends on the selection of appropriate candidate antigens and their immunodominant epitopes. The prediction of appropriate antigenic epitopes of a target protein by immunoinformatic methods is extremely important for designing a multi-epitope vaccine. Immunoinformatic tools predict and screen the immunogenic T- and B-cell epitopes of the target antigens, then design peptides rich in epitopes or overlapping epitopes. For the prediction of B-cell epitopes, multiple alignments of the target antigen are initially carried out using software from the European Bioinformatics Institute website (http://www.ebi.ac.uk/Tools/clustalw2). Then, the structure, hydrophilicity and flexibility, and transmembrane domains of the target antigen are predicted and analyzed by methods including GOR, Hoop and Woods and artificial neural network (http://strucbio.biologie.uni-konstanz.de). Antigenic propensity value is further evaluated using the Kolaskar and Tongaonkar approach (http://bio.dfci.harvard.edu/Tools/antigenic.pl). Finally, the B-cell-dominant epitope is determined by comprehensive analysis and comparison, and T-cell epitopes including MHC-I restriction CTL and MHC-restriction Th epitopes are predicted using the SYFPEITHI network database (http://www.syfpeithi.de/Scripts/MHCServer.dll/EpitopePrediction.htm). All the above-mentioned programs are provided on the EXPASY server (http://www-.expasy.org/tools).

Immunoinformatics methods can help to predict and screen appropriate epitopes for designing an efficacious multi-epitope vaccine.

HER2 overexpression plays a pivotal role in breast cancer patients and is associated with poorer overall survival. The HER2 overexpression has been reported to have aggressive biological properties, and promotes cell proliferation and survival. Phosphorylation of the tyrosine kinase domain of HER2 by homodimerization or heterodimerization promotes cell proliferation and survival signaling. Currently, monoclonal antibodies (trastuzumab and pertuzumab), antibody-drug conjugates, and tyrosine kinases (lapatinib, neratinib, and tucatinib) have been developed as HER2 targeted therapeutics. However, development of acquired resistance is inevitable in HER2 positive breast cancer patients. The underlying mechanism of resistance to HER2 targeted therapeutics involve HER2, EGFR, and PI3K, but the mechanisms for overcoming tolerance and related therapies are still limited.

HSP90 has pivotal role in breast cancer biology. HSP90 is a molecular chaperone that is involved in many different cellular pathways. So far, more than 200 client proteins are known to be regulated by HSP90. The molecular chaperone HSP90, which has the unique ability to reduce the activity of multiple receptors, kinases and transcription factors known to be involved in human cancer, has been identified as an important therapeutic target in many studies. As a promising therapeutic target for cancer, HSP90 inhibitors have been developed and tested in clinical trials. Despite promising efficacy, further clinical development was stopped due to toxicities. Thus, safer strategies, such as immunologic therapeutics, might be a better way to target HSP90. In a recent study, the amplification and higher expression of HSP90 were associated with poorer overall survival in patients with higher risk of recurrence in HER2+ and HER2−/ER+ breast cancer subtypes. Liu et al confirmed that autoantibodies of HSP90 were detected in 36.8% breast cancer patient, but not in healthy control or patient with benign breast tumor. Thus, HSP90 can be considered a novel therapeutic target for breast cancer immunotherapy.

Figure 1:
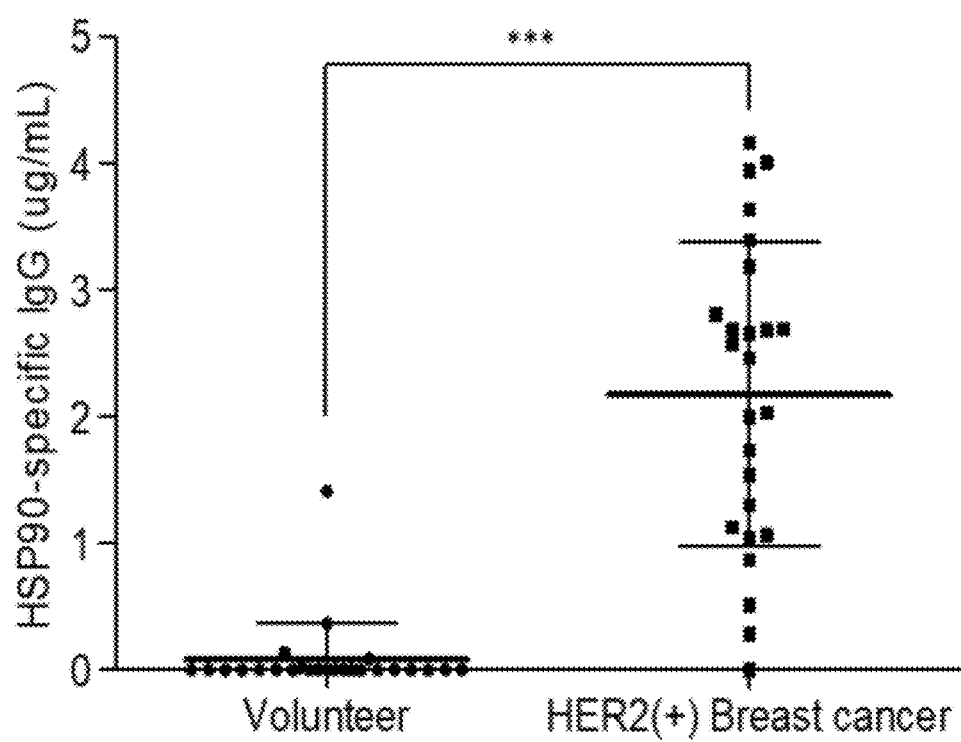

An aspect of the present invention aimed to determine whether HSP90 is a natural tumor antigen in patients of HER2 type breast cancer. As a result, level of HSP90-specific antibody was significantly higher in HER2-positive breast cancer patients compared with volunteer donors (FIG. 1). Therefore, tumor antigen-specific antibody immunity is distinctly associated with antigen-specific T cells response in HER2 positive breast cancer patients.

In general, epitope prediction methods include data driven methods for predicting peptide-MHC binding are based on peptide sequences that are known to bind MHC I and II molecules, and now include the use of specialized epitope database. Peptide-MHC binding predictions using a sequence motif reflects the amino acid preferences of MHC I and II molecules, and a motif matrix that can assess the contribution of each peptide position to binding with the MHC molecule. However, it was shown that non-anchor residues bind to a given MHC molecule. In addition, motif matrix was derived without considering the binding affinity, and the resulting peptide score was inaccurate in predicting binding affinity. Most MHC I peptide ligands have 9 residues. In contrast, the peptide-binding groove of the MHC II molecule is open so that the N- and C-terminals of the peptide could extend beyond the binding groove. Consequently, only 9 residue cores (peptide binding cores) enter the MHC II binding grooves, but the length of the MHC II-binding peptides varies (9-22 residues). As a result, the peptide-binding prediction for MHC II molecules has been able to predict stronger and longer peptides than that of MHC I molecules.

Figure 2:
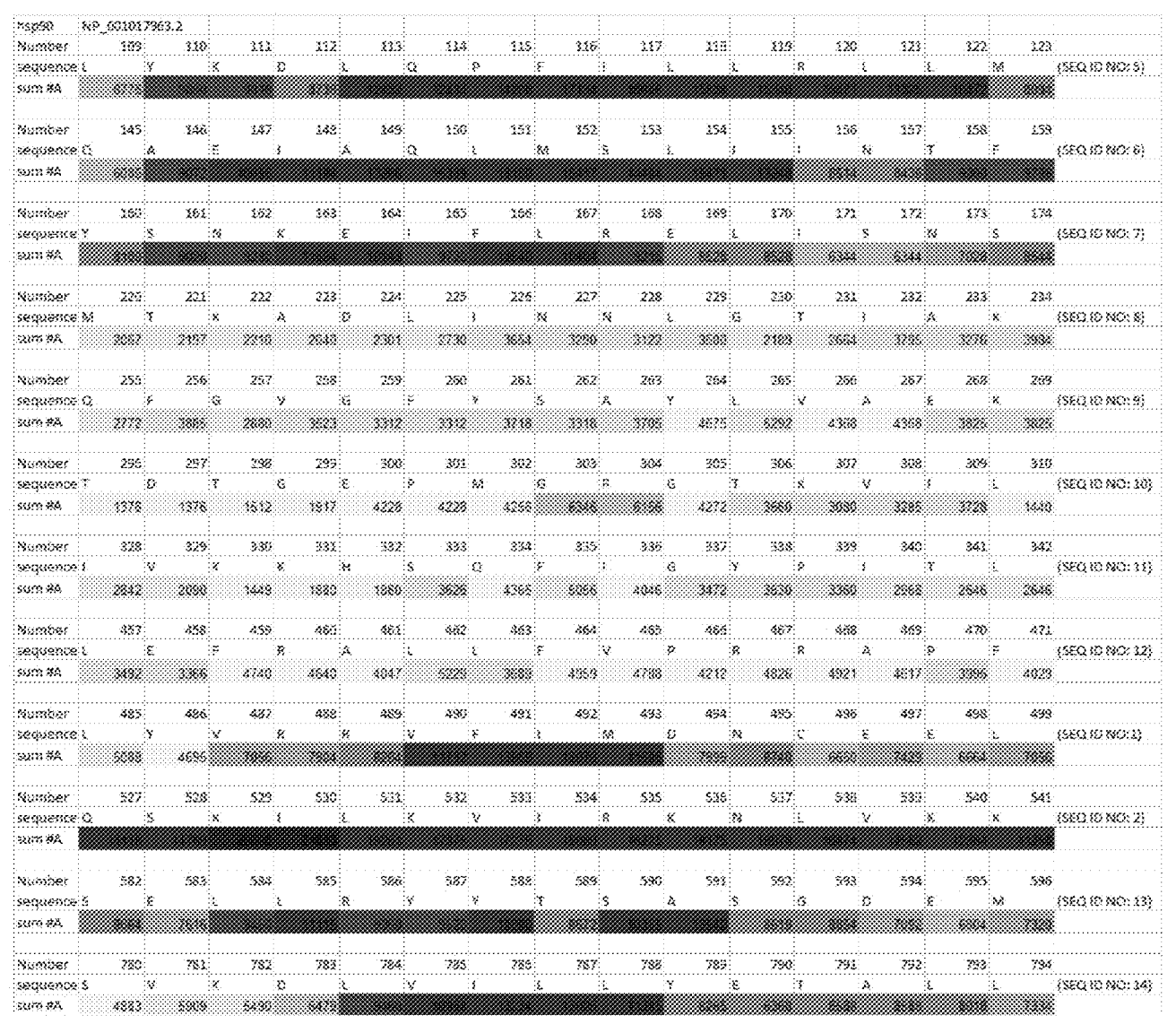
Figure 4A:
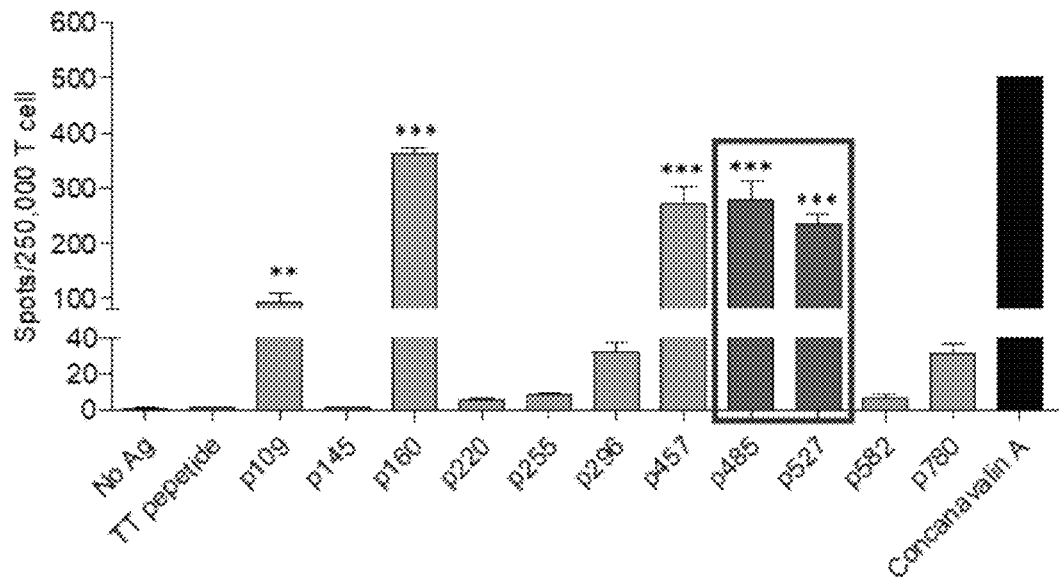
Figure 4B:
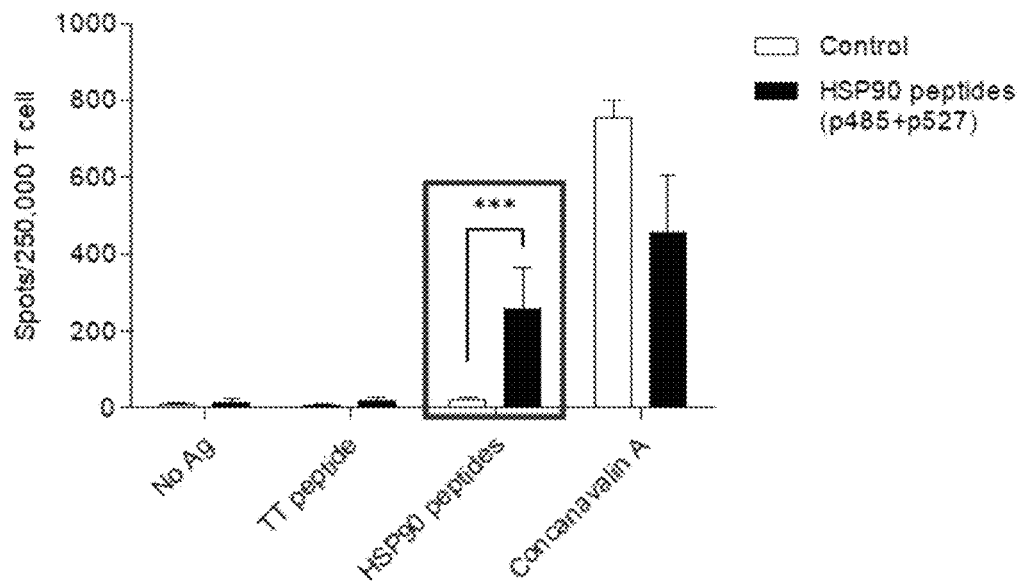

In this study, a scoring system developed in a previous study was used to identify the best MHC class II epitopes. Based on this system, 15-mer HSP90 peptide sequences were selected by assigning scores to each amino acid from 5 class II epitope prediction algorithms and the most promiscuously high-affinity class II binding sequences to the most common human HLA molecules (FIG. 2). The selected 11 peptides showed more than 80% homology with human and murine proteins. The selected HSP90 peptides were screened for Th1 or Th2 immunity in human PBMC from volunteer donor by ELISPOT assay as representative Th1 cytokine, IFN-γ and Th2 cytokine, IL-10. As a result, p485 and p527 peptides were evaluated as promising epitope without Th2 immunity while inducing the strongest Th1 immunity. To confirm their immunogenicity, 11 selected HSP90 peptides were evaluated for antigen-specific T cell responses by IFN-γ ELISPOT assay in mouse model. As a results, the cytokine IFN-γ producing Th1 cells of selected p485 and p527 from human PBMCs increased the most, and showed significant immunogenicity even when subjected to combined administration (FIGS. 4A and 4B). Furthermore, this study investigated whether immunity to HSP90 would affects tumor growth using a neu-transgenic mouse model. A neu-transgenic mouse model was engineered to express non-activating rat neu under the control of the mouse mammary tumor virus promoter/enhancer. The neu-transgenic mouse model is a surrogate for HER2-type human breast cancer. In addition, a mouse mammary carcinoma cell line was established from a spontaneous tumor in a neu-transgenic mouse model and used in an animal study. HSP90 peptides showed anti-tumor rejection responses and increased HSP90-specific T cell responses. Thus, the predicted HSP90 peptides affect anti-tumor rejection effect by increasing the antigen-specific T cell responses in vivo.

Figure 6A:
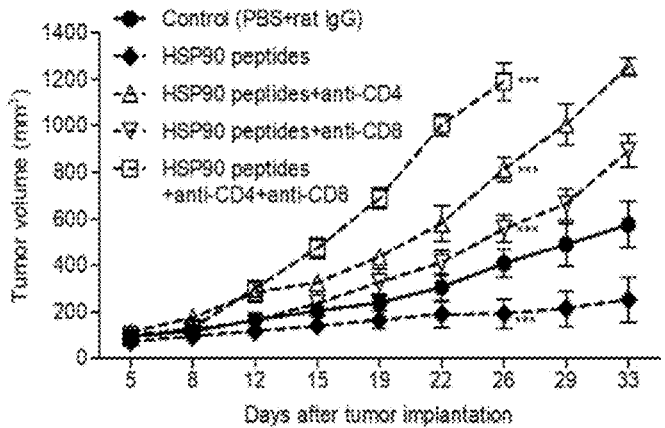
Figure 6B:
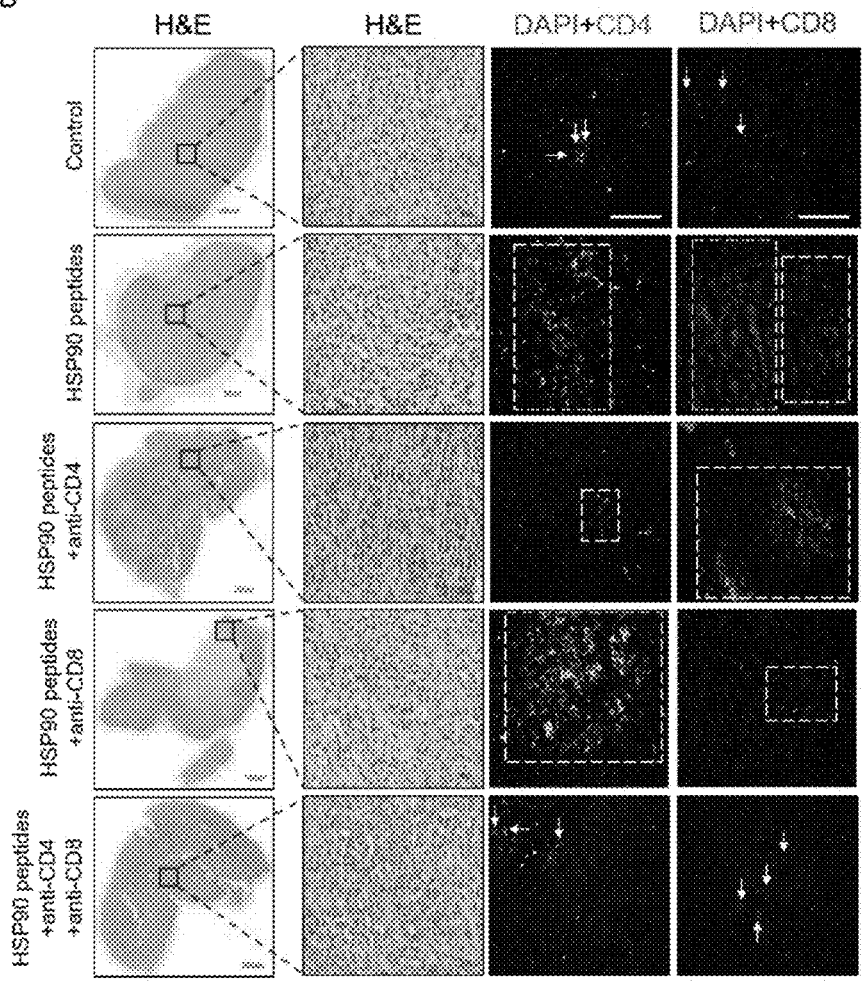

The HSP90 peptide vaccine shows an improved anti-tumor effect in a mouse model. However, the type of T cells activated as part of the immune response to HSP90 peptides are not known. To understand this, the present inventors performed depletion of CD4+ or CD8+ T cells with immunization of HSP90 peptide in mouse model to investigate the relationship between the regulation of T cells responses and HSP90 peptide immunization. The efficacy was most reversed by depletion of CD4+ T cells, but depletion of CD8+ T cells was only partially reversed efficacy (FIGS. 6A and 6B). Thus, these results suggest that the HSP90 peptide vaccine works mainly through CD4+ T cells.

Figure 7A:
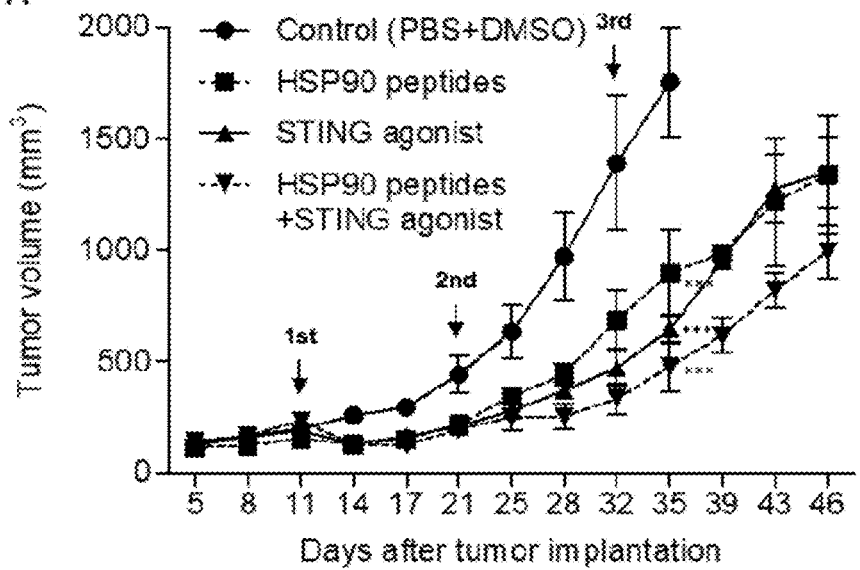
Figure 7:
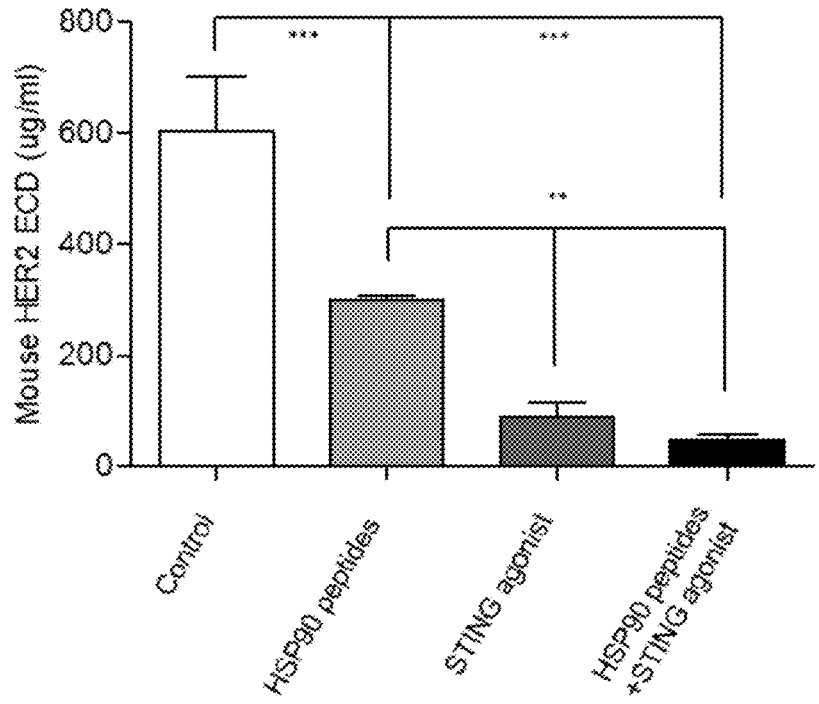
Figure 7C:
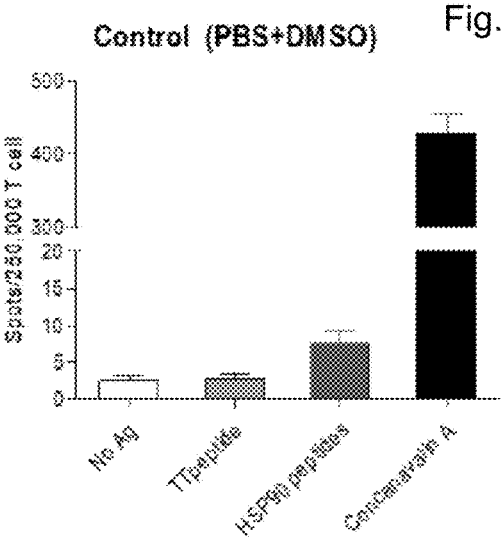
Figure 7D:
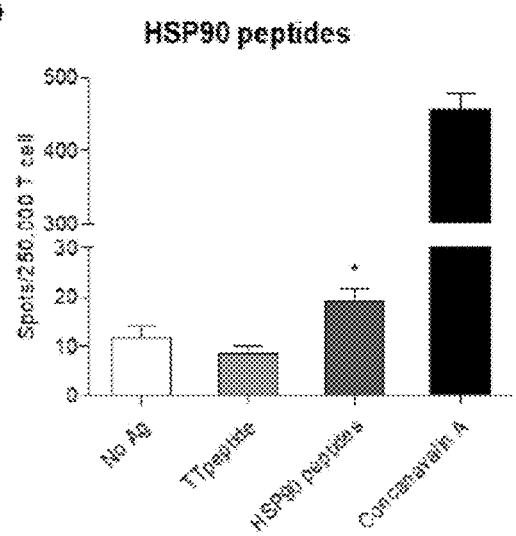
Figure 7E:
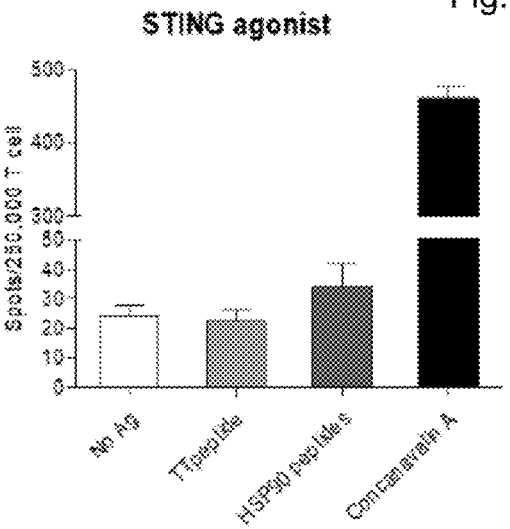
Figure 7F:
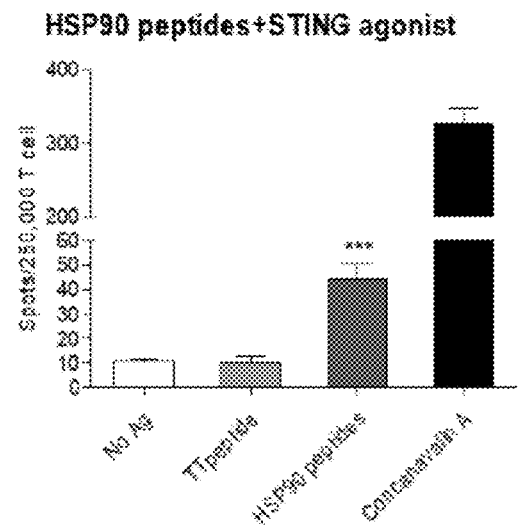
Figure 9A:
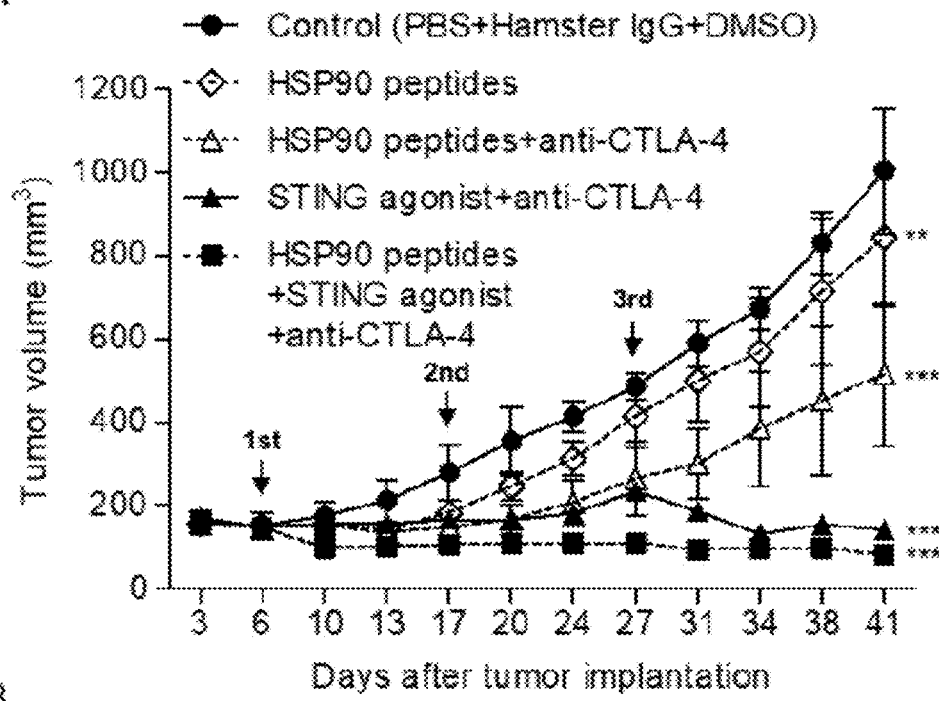
Figure 9B:
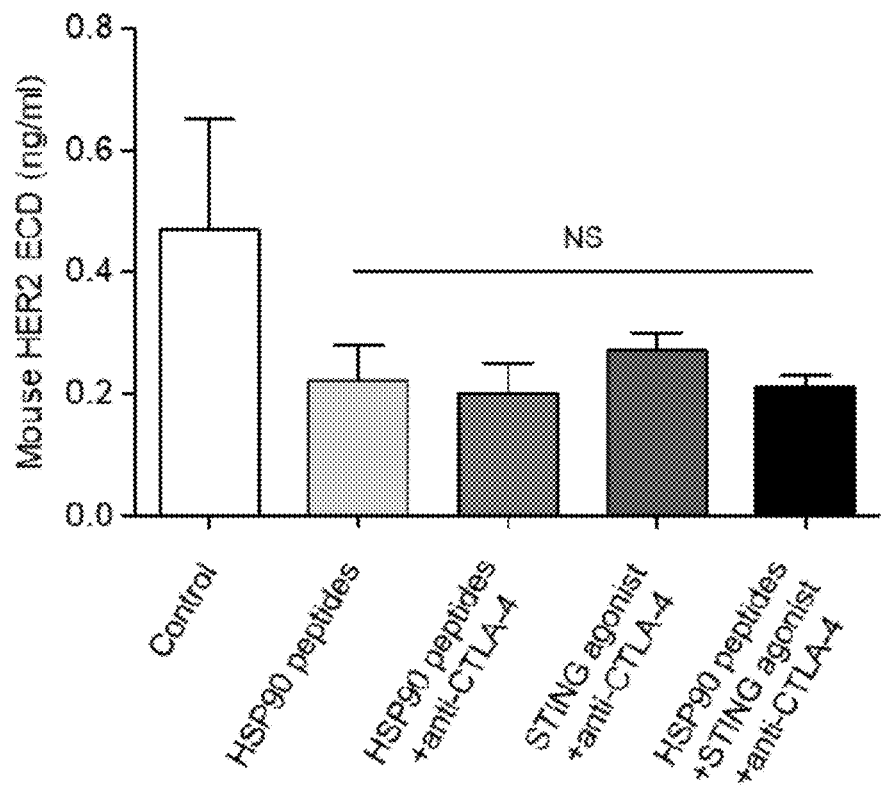
Figure 9C:
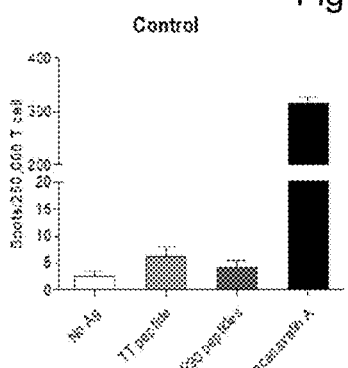
Figure 9D:
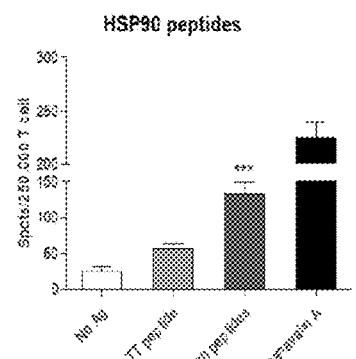
Figure 9E:
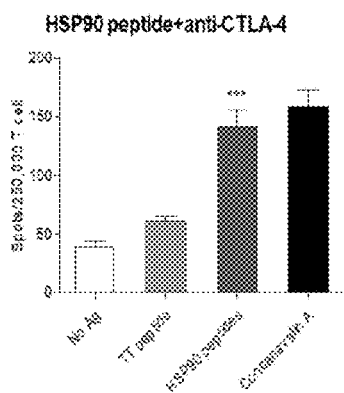
Figure 9F:
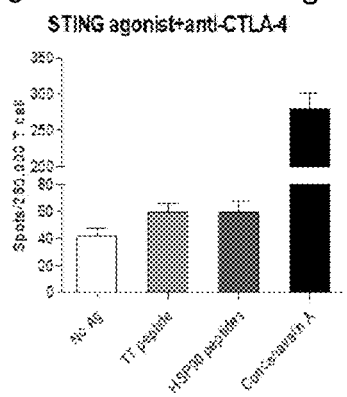
Figure 9G:
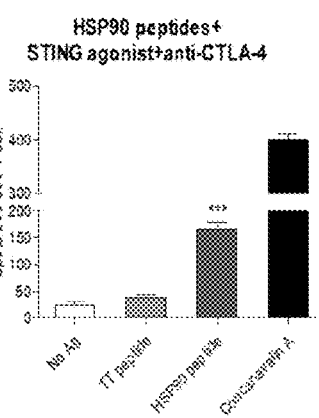
Figure 10A:
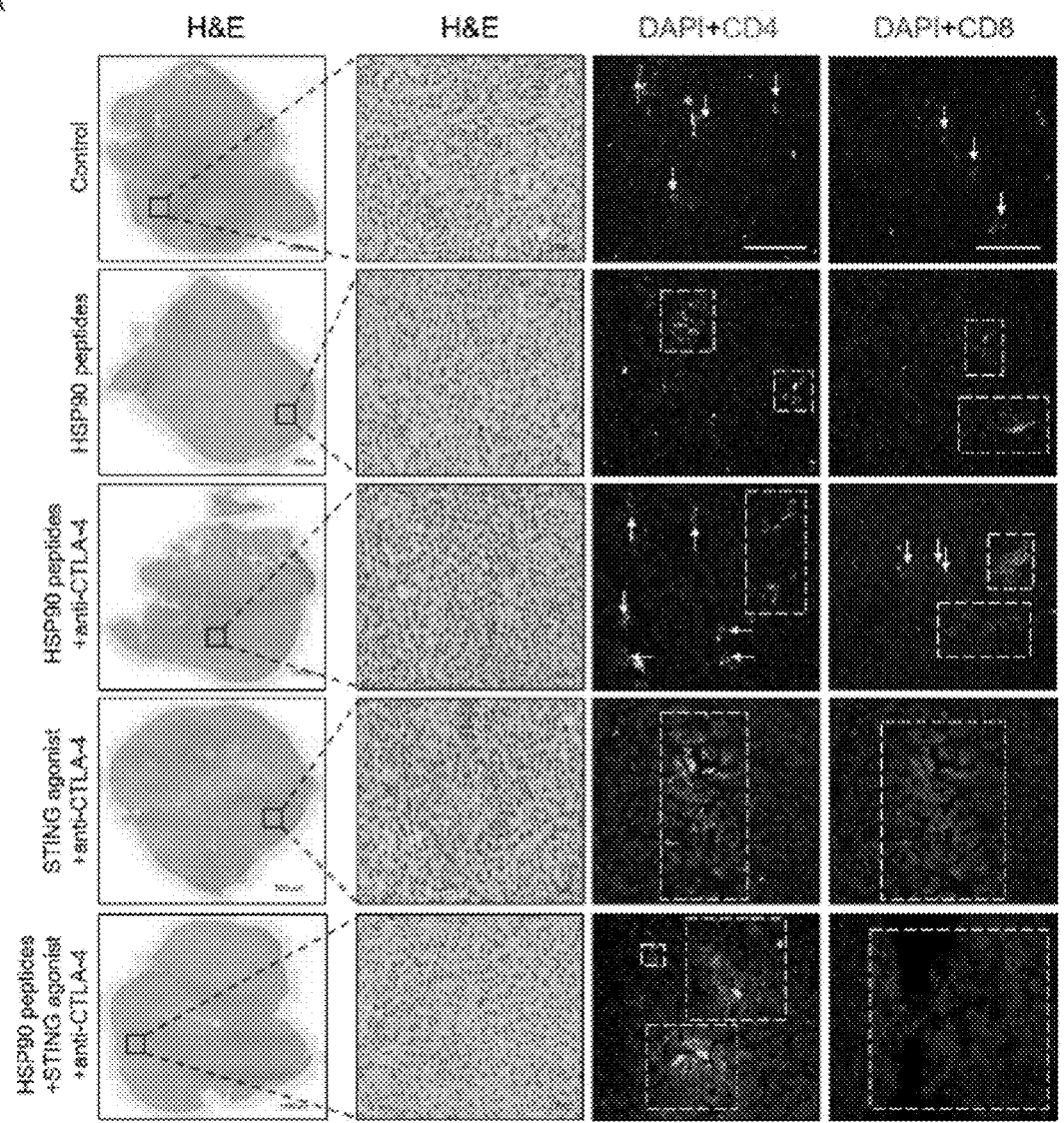
Figure 10B:
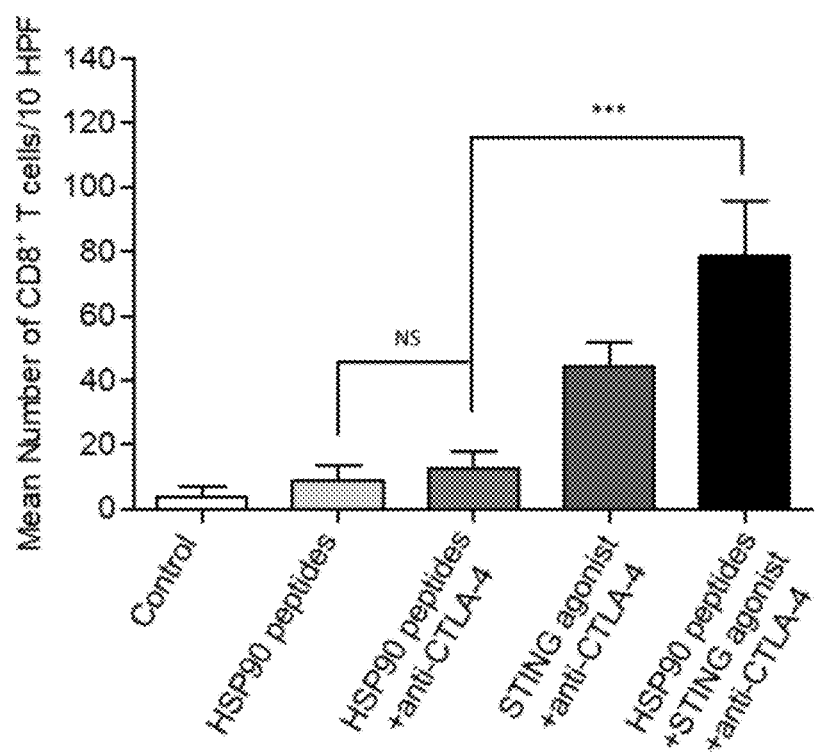
Figure 10:
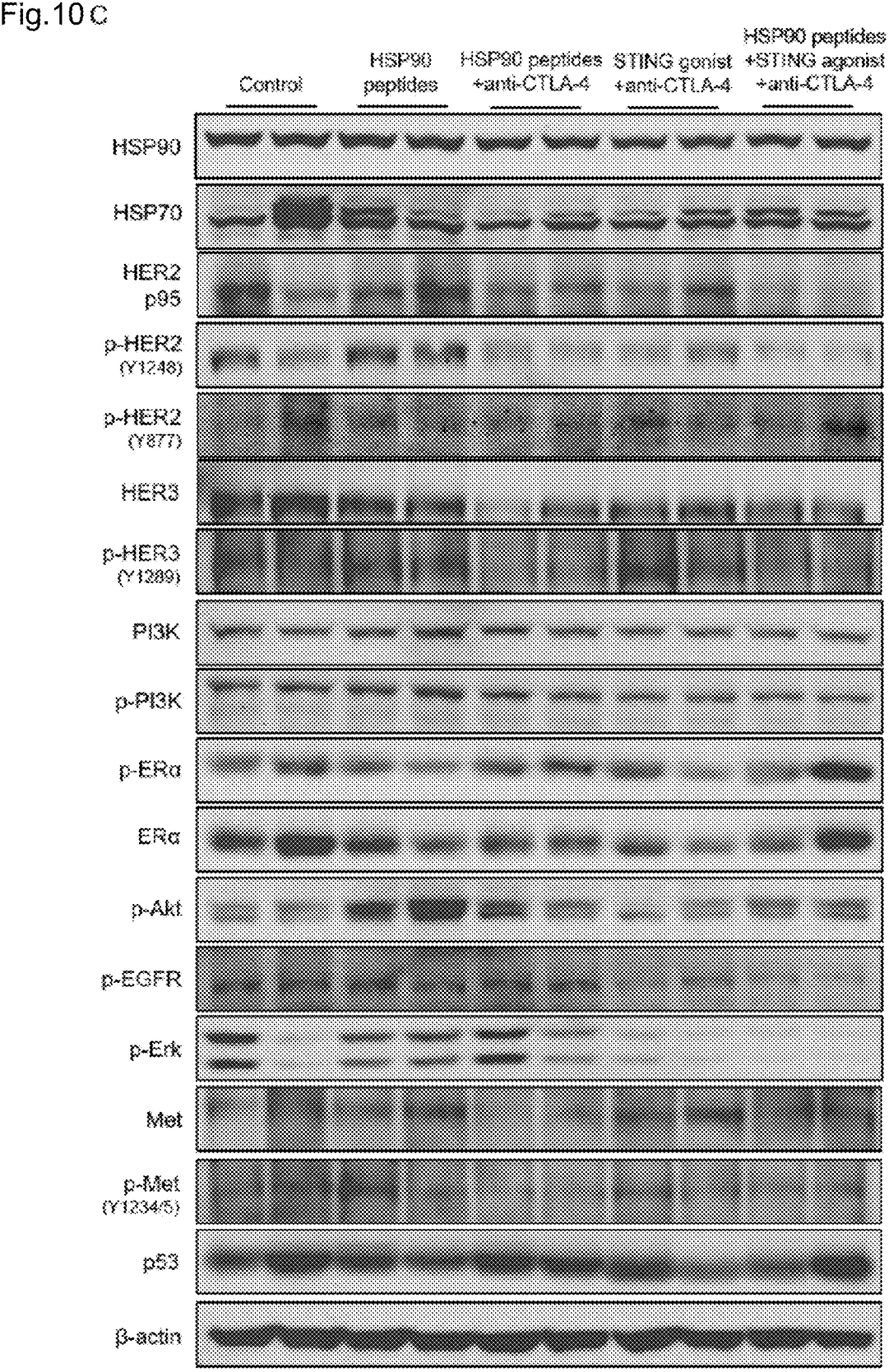

The tumor vaccine alone is not sufficient to suppress tumor growth, especially in metastasis setting. In the present invention, more potent treatment strategy was needed to increase the efficacy of the HSP90 vaccine. Recent studies have reported that STING signaling pathway enables promotion or induction innate and adaptive immune responses. In many studies, STING pathway has been reported to generate innate and adaptive immune responses in a variety of additional in vitro and in vivo tumor model. STING activation induces production of cytokines such as type I IFNs. Type I IFN promotes induction of type I Th1 cell response and cytotoxic T cell response. Longhi et al have also been reported that type I IFN promotes activation and function of dendritic cells, and probably facilitates antigen-presentation to CD4+ T cells and CD8+ T cells. Recent studies have reported that STING-deficient mice have more sensitivity to tumor formation, reduced anti-tumor T cells immunity and attenuated response to immunotherapy such as immune checkpoint inhibitors. In addition, the combination of CTLA-4 blockade with HSP90 vaccine was investigated to enhance anti-tumor efficacy in metastatic setting. Anti-CTLA-4 antibody has also been widely also used with other immunotherapy for the treatment of many cancer. In many studies, CTLA-4, an immune checkpoint blockade, eliminated the immunosuppressive propagation of T-cell activation, demonstrating that tumor-responsive T cells activate regulatory mechanisms and enable effective anti-tumor responses. Thus, innate immune sensing through STING signaling pathway is critical for enhancing optimal anti-tumor effect by checkpoint blockade therapies. The STING agonist and anti-CTLA-4 Ab may be considered suitable for combination with a vaccine. As expected, the best anti-tumor response was observed to be effective in the combination of STING agonist after HSP90 peptides immunization. Thus, IFN-γ ELISPOT showed the best anti-tumor effects for the combination therapy with HSP90 vaccine and STING agonist, which showed better HSP90-specific T cells responses (FIG. 7). In addition, the percentage survival rate of mice showed improvement in response to the combination therapy with HSP90 peptides and STING agonist. Furthermore, the triple combination with HSP90 peptides/STING agonist/anti-CTLA-4 Ab showed the best anti-tumor effect in a neu-transgenic mouse model. HSP90-specific T cell responses were significantly enhanced in the triple combination of HSP90 peptides/STING agonist/anti-CTLA-4 Ab (FIGS. 9A-9G). As results of investigating the immune microenvironment, the number of infiltrated CD4+ and CD8+ T cells in the tumor observed increased in the triple combination of HSP90 peptides/STING agonist/anti-CTLA-4 Ab (FIGS. 10A-10C). These results suggest that the combination of STING agonist and anti-CTLA-4 Ab is a possible therapeutic strategy to maximize the effect of HSP90 peptides in HER2-positive breast cancer metastatic setting.

Many studies have reported that high serum levels of HER2 ECD are associated with poor prognosis in advanced breast cancer patients. In search of convenient biomarker for in vivo study, HER2 ECD have identified as indicators of the biological activity that are derived from or are regulated by HSP90 client protein. As results, HER2 ECD decreased after vaccination of HSP90 peptides in vivo. Of note, HER2 ECD was significant reduced by combination with STING agonist and/or anti-CTLA-4 Ab after immunization of HSP90 peptides in neu-transgenic mice. Further analysis is needed for reliable results on the biology activity indicators of HSP90 peptides in breast cancer.

Figure 11A:
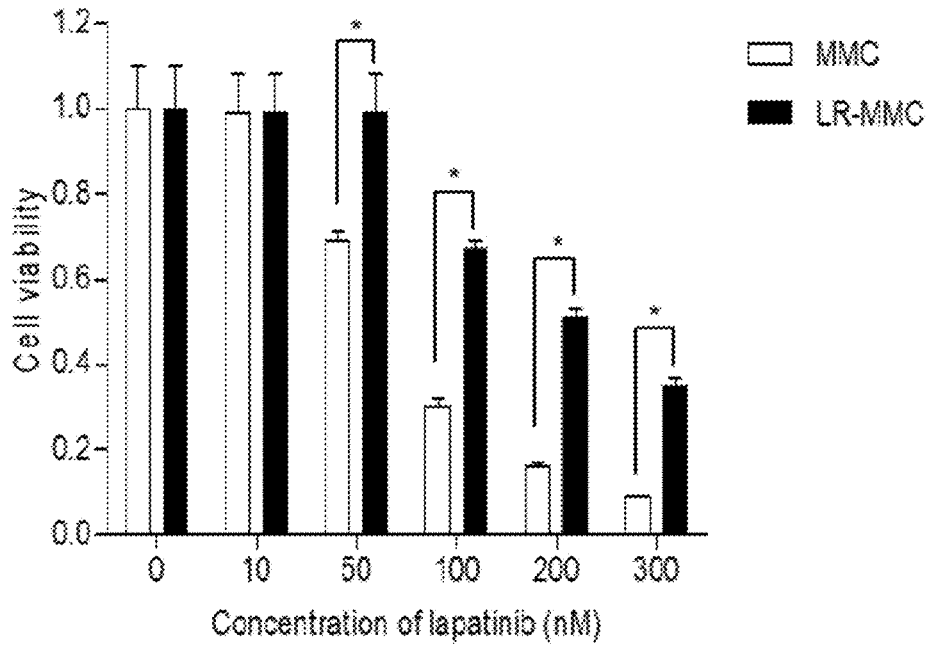
Figure 11B:
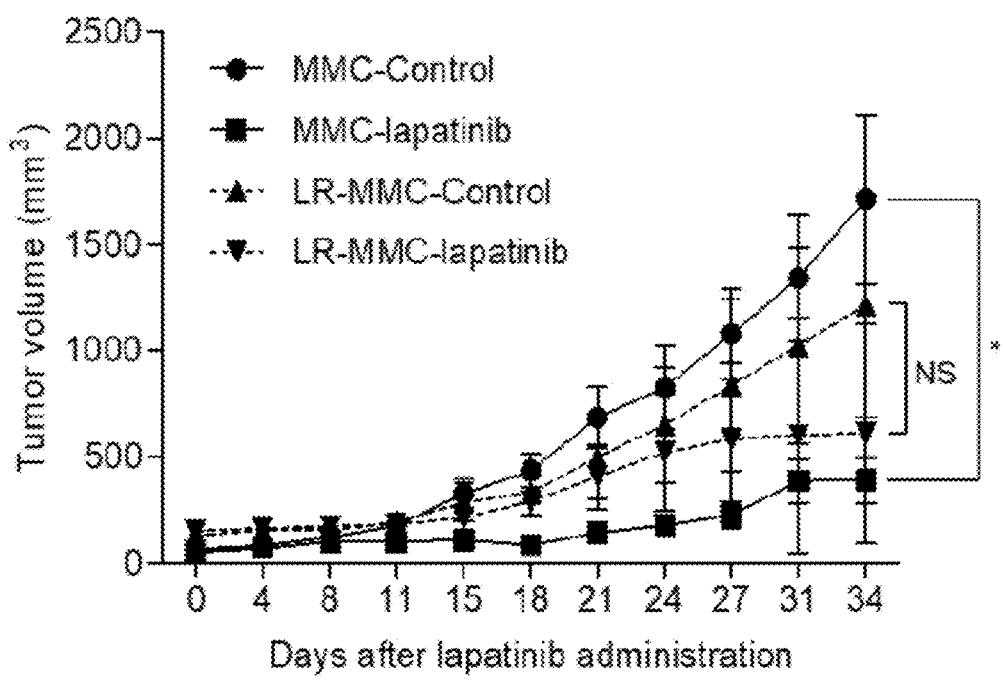
Figure 12:
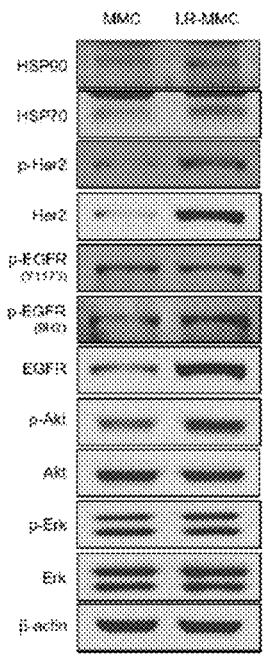
Figure 12:
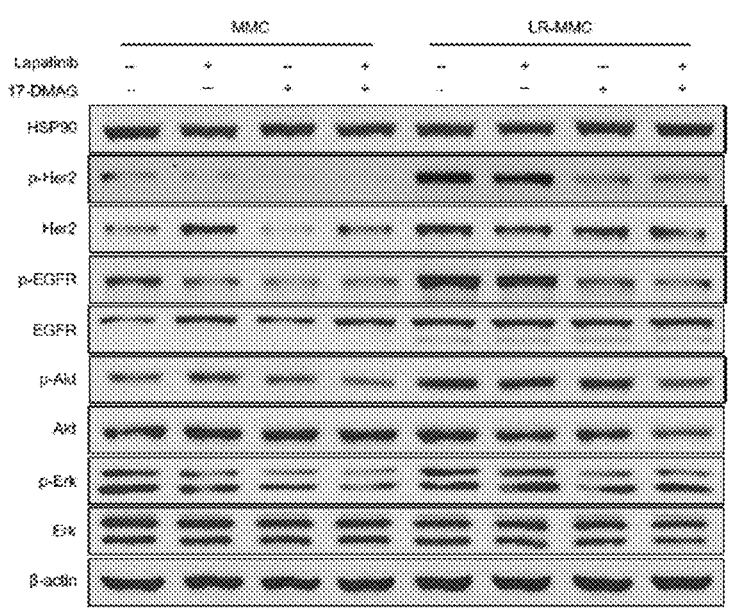

This is because resistance to treatment with anti-HER2 TKI or antibody frequently occurs in clinical practice in metastatic settings. In particular, for test that overcome the resistance of HER2 TKI or antibody treatment in immunological therapy, this study has easily established a HER2 TKI resistant mouse and cell line models. Established LR-MMC cells showed resistance after treatment with lapatinib in a mouse model (FIGS. 11A and 11B). In addition, the mechanism for acquired resistance of lapatinib in lapatinib-resistant MMC cells in vitro was confirmed, and had a positive effect upon the combination treatment of HSP90 inhibitors (FIGS. 12A and 12B). Based on the results demonstrated in vitro, this study evaluated whether the combined effect of lapatinib/HSP90 peptides/STING agonist/anti-CTLA-4 Ab was efficacious in overcoming resistance to lapatinib in vivo. As a result, lapatinib group was stilled resistance to lapatinib, but it overcame the resistance to lapatinib in the combination with lapatinib/HSP90 peptides/STING agonist/anti-CTLA-4 Ab group (FIGS. 13A-13H). With the same results as in the previous study, it was found that the combined effect of the HSP90 vaccine and other drugs was remarkably good in HER2 TKI resistant mouse and cell line model.

Figure 13A:
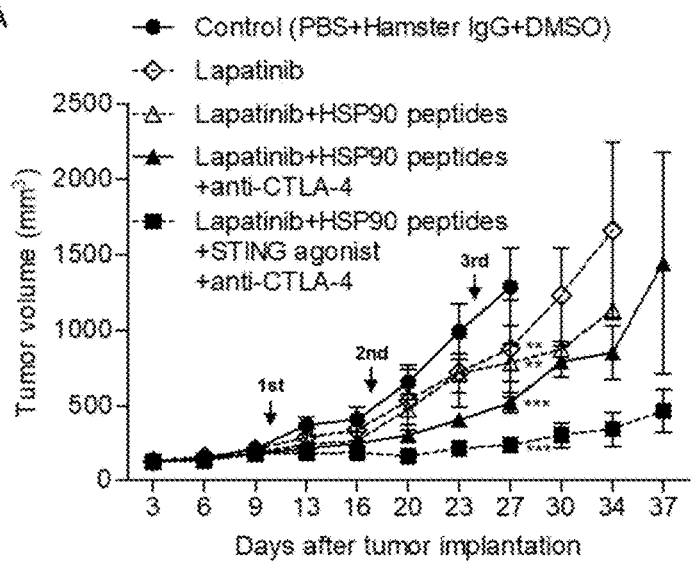
Figure 13B:
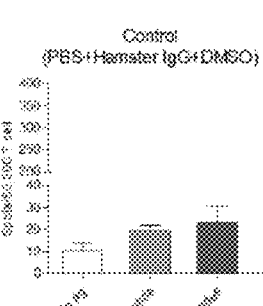
Figure 13C:
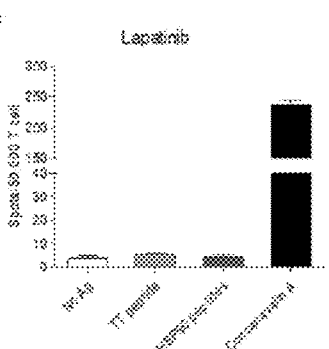
Figure 13D:
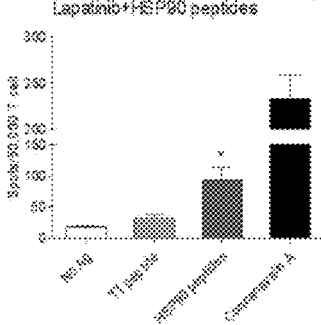
Figure 13E:
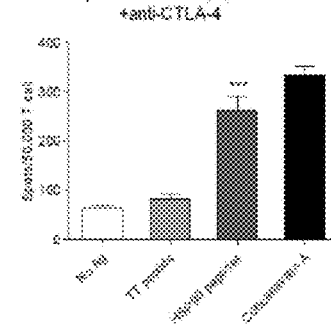
Figure 13F:
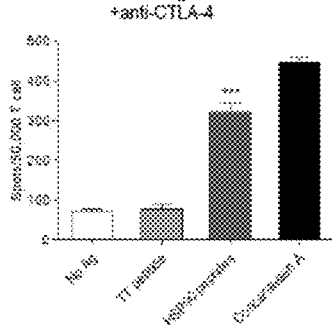
Figure 13G:
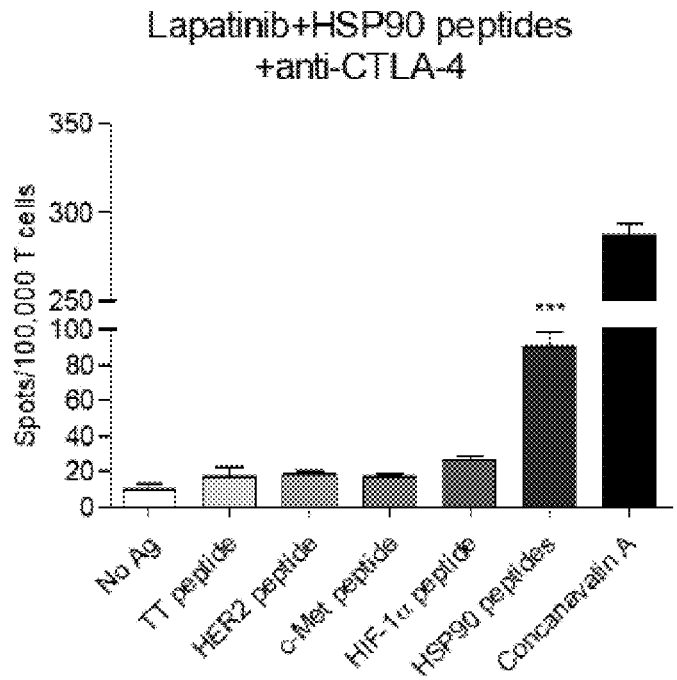
Figure 14A:
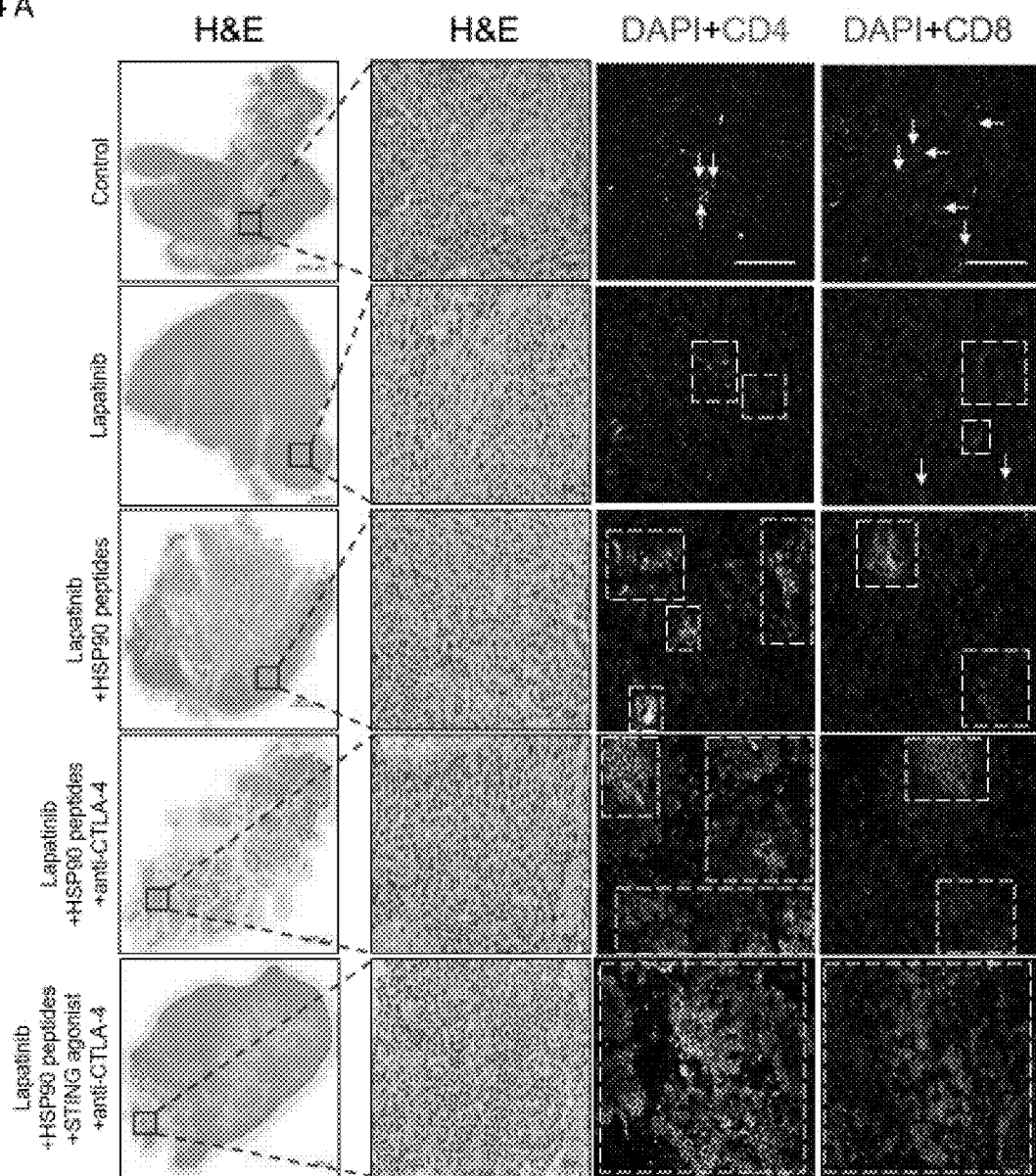

In many immune-related studies, antigen-spreading has been observed in relation to autoimmunity and infectious diseases. Cancer immunotherapy has an immune response against a specific target antigen, but is known to work partially through antigen-spreading. Epitope-spreading refers to the process by which other antigen epitopes that are non-cross-reactive independent of a specific inducing epitope, are additionally targeted for a sustained immune response. In a recent study, epitope spreading has been shown to be associated with anti-tumor effects in peptide-based cancer immunotherapy, and has been found to be of considerable advantage in improving the therapeutic effects. Therefore, to investigate the epitope-spreading of the other peptides, it was evaluated for HER2, c-MET and HIF-1α peptides by IFN-γ ELISPOT assay. Surprisingly, the epitope-spreading was not observed in response to the combination therapy with lapatinib/HSP90 peptides/anti-CTLA-4 Ab. However, the addition of STING agonist significantly increased the antigen-specific T cell responses to HER2 and HIF-1α peptides (FIGS. 13G and H). These results suggest that the HSP90 peptides may enable epitope-spreading of the other peptides in addition to the STING agonist as the immune system response to generate innate and adaptive anti-tumor immunity by type I IFN. Future investigations will address the propensity of antigen-specific T cells by analyzing the characteristics of T cell receptor repertoires in combination with Iapatnib/HSP90 peptides/STING agonist/anti-CTLA-4 Ab to understand the immune response to HSP90 peptide vaccine in mice. Furthermore, the number of infiltrated CD4+ and CD8+ T cells in the tumor was most increased in response to the combination therapy with lapatinib/HSP90 peptides/STING agonist/anti-CTLA-4 Ab in the immune microenvironment (FIGS. 14A and 14B). Accordingly, understanding the T cell infiltration in the immune microenvironment in tumors, will confirm the propensity for quantification of immune cells by fluorescent multiplex immunohistochemical analysis. Taken together, these results demonstrate that a combination therapy of HSP90 peptides with STING agonist and anti-CTLA-4 Ab is a promising immunotherapeutic strategy targeting anti-HER2 TKI resistant breast cancer.

In conclusion, a combination therapy of HSP90 peptides with STING agonist and anti-CTLA-4 Ab is a promising immunologic strategy in lapatinib-resistant HER2 type advanced breast cancer and various cancer patients. The present invention has provided the first preclinical evidence supporting the mechanism of action of HSP90 peptides vaccine that have a distinct potential to improve treatment of breast cancer.

Briefly, in an embodiment of the present invention, 12 15-mer peptide sequences that are expected to have good binding affinity to the most common MHC class II allele using 5 algorithm programs for Hsp 90 full sequences were selected. Thereafter, two types of epitopes having good binding affinity to the MHC class II allele and excellent antitumor effect were obtained. In the present invention, it was confirmed that the vaccine composition containing the epitope polypeptide of heat shock protein 90 (Hsp90) represented by the amino acid sequence of SEQ ID NO: 1 or 2 induces the Th1 immune response and has excellent antitumor effects.

Accordingly, in one aspect, the present invention provides a multi-epitope vaccine(s) comprising an epitope represented by the amino acid sequence of SEQ ID NO: 1 and/or an epitope represented by the amino acid sequence of SEQ ID NO: 2.

An epitope, also known as antigenic determinant, is the part of an antigen that is recognized by the immune system, specifically by antibodies, B cells, or T cells. For example, the epitope is the specific piece of the antigen to which an antibody binds. The part of an antibody that binds to the epitope is called a paratope. Although epitopes are usually non-self proteins, sequences derived from the host that can be recognized (as in the case of autoimmune diseases) are also epitopes.

T cell epitopes are presented on the surface of an antigen-presenting cell, where they are bound to MHC molecules. In humans, professional antigen-presenting cells are specialized to present MHC class II peptides, whereas most nucleated somatic cells present MHC class I peptides. T cell epitopes presented by MHC class I molecules are typically peptides between 8 and 11 amino acids in length, whereas MHC class II molecules present longer peptides, 13-17 amino acids in length, and non-classical MHC molecules also present non-peptidic epitopes such as glycolipids.

Herein, the multi-peptide vaccine or the multi-epitope vaccine with a broader meaning can be used interchangeably. For example, the "multi-peptide vaccine" may be a vaccine containing two or more peptide epitopes. The multi-peptide vaccine or the multi-epitope vaccine of the present invention may be characterized in that it contains the epitope of heat shock protein 90 represented by the amino acid sequence of SEQ ID NO: 1 and/or the epitope of heat shock protein 90 represented by the amino acid sequence of SEQ ID NO: 2.

In another aspect, the present invention provides a multi-epitope vaccine gene comprising a nucleic acid encoding an epitope represented by the amino acid sequence of SEQ ID NO: 1 and/or a nucleic acid encoding an epitope represented by the amino acid sequence of SEQ ID NO: 2.

For example, the nucleic acid encoding the epitope represented by the amino acid sequence of SEQ ID NO: 1 is represented by the nucleotide sequence of SEQ ID NO: 3 and/or the nucleic acid encoding the epitope represented by the amino acid sequence of SEQ ID NO: 2 is represented by the nucleotide sequence of SEQ ID NO: 4.

In another aspect, the present invention relates to a recombinant vector containing the gene and a recombinant microorganism into which the gene or the recombinant vector has been introduced.

In another aspect, the present invention relates to a method for producing the polypeptide comprising the steps of (a) culturing the recombinant microorganism to produce the polypeptide; and (b) obtaining the produced polypeptide.

Expression of the recombinant multi-epitope protein from the constructed multi-epitope vaccine gene can be optimized to maximize its production in *E. coli*.

In the present invention, the vector refers to a DNA sequence linked to a suitable control sequence so that the target protein can be expressed in a suitable host cell. The control sequence may include a promoter capable of initiating transcription, any operator sequence for regulating such transcription, a sequence encoding a suitable mRNA ribosome binding site, and a sequence controlling the termination of transcription and translation. It can be manufactured in various ways, depending on the purpose. The promoter of the vector can be constitutive or inducible. Vectors can be transformed into a suitable host and then replicate or function independently of the host genome, or can be integrated into the genome itself.

The vector used in the present invention is not particularly limited as long as it can replicate among host cells, and any vector known in the art may be used. Examples of commonly used vectors include natural or recombinant plasmids, phagemids, cosmids, viruses and bacteriophages. For example, pWE15, M13, λMBL3, λMBL4, λIXII, λASHII, λAPII, λt10, λt11, Charon4A, and Charon21A can be used as a phage vector or a cosmid vector, and as a plasmid vector, pBR system, pUC system, pBluescript II system, pGEM system, pTZ system, pCL system and pET system can be used. The vector usable in the present invention is not particularly limited, and a known expression vector may be used.

The term "expression control sequence" means a DNA sequence essential for the expression of a coding sequence operably linked in a particular host organism. Such regulatory sequences include promoters for effecting transcription, any operator sequences for regulating such transcription, sequences encoding suitable mRNA ribosome binding sites, and sequences that regulate termination of transcription and translation. For example, regulatory sequences suitable for prokaryotes include a promoter, optionally an operator sequence, and a ribosome binding site. Regulatory sequences suitable for eukaryotic cells include promoters, polyadenylation signals and enhancers. The factor that most affects the amount of gene expression in the plasmid is the promoter. As a promoter for high expression, an SRα promoter, a cytomegalovirus-derived promoter, and the like are preferably used.

In order to express the DNA sequence of the present invention, any of a wide variety of expression control sequences can be used in the vector. Examples of useful expression control sequences include early and late promoters of SV40 or adenovirus, lac system, trp system, TAC or TRC system, T3 and T7 promoters, major operator and promoter regions of phage lambda, regulatory regions of FD protein, promoters for 3-phosphoglycerate kinase or other glycolytic enzymes, promoters of the phosphatase, for example Pho5, promoters of the yeast alpha-crossing system, and other sequences of constructs and inductions known to regulate the expression of genes of prokaryotic or eukaryotic cells or their viruses, and various combinations thereof. The T7 RNA polymerase promoter φ10 can be usefully used to express protein NSP in E. coli.

Nucleic acids are "operably linked" when placed in a functional relationship with another nucleic acid sequence. It may be a gene and regulatory sequence(s) linked in a manner that allows gene expression when an appropriate molecule (e.g., a transcriptional activating protein) is bound to the regulatory sequence(s). For example, DNA for a pre-sequence or secretory leader is operably linked to the DNA for a polypeptide when expressed as a whole protein that participates in the secretion of the polypeptide; the promoter or enhancer is operably linked to the coding sequence if it affects the transcription of the sequence; the ribosome binding site is operably linked to the coding sequence if it affects the transcription of the sequence; or the ribosome binding site is operably linked to a coding sequence when arranged to facilitate translation. In general, "operably linked" means that the linked DNA sequence is in contact, and, in the case of a secretory leader, is brought into contact and within the reading frame. However, the enhancer does not need to be in contact. The ligation of these sequences is carried out by ligation (linkage) at convenient restriction enzyme sites. If such a site does not exist, a synthetic oligonucleotide adapter or linker according to a conventional method is used.

The term "expression vector" as used herein is a recombinant carrier into which a fragment of a heterologous DNA is inserted, and generally refers to a fragment of double-stranded DNA. Here, heterologous DNA refers to DNA that is not naturally found in host cells. Once in the host cell, the expression vector can replicate independently of the host chromosomal DNA and several copies of the vector and its inserted (heterologous) DNA can be generated.

As is well known in the art, in order to increase the expression level of a transfected gene in a host cell, the gene must be operably linked to transcriptional and translational expression control sequences that exert a function in the selected expression host. Preferably, the expression control sequence and the corresponding gene are included in a single expression vector containing a bacterial selection marker and a replication origin. When the expression host is a eukaryotic cell, the expression vector should further contain an expression marker useful in the eukaryotic expression host.

In order to express the gene encoding the polypeptide of the present invention, a wide variety of expression host/vector combinations can be used. Expression vectors suitable for eukaryotic hosts contain expression control sequences derived from, for example, SV40, bovine papillomavirus, anenovirus, adeno-associated virus, cytomegalovirus and retrovirus. Expression vectors that can be used for bacterial hosts include bacterial plasmids obtained from E. coli such as pBluescript, pGEX2T, pUC vector, colE1, pCR1, pBR322, pM89 and derivatives thereof; plasmids having a wider host range such as RP4; phage DNA, which can be exemplified by a wide variety of phage lambda derivatives such as λgt10 and λgt11, NM989; and other DNA phages such as M13 and filamentous single-stranded DNA phage. Expression vectors useful for yeast cells are 2μ plasmids and derivatives thereof. A vector useful for insect cells is pVL941

Host cells transformed or transfected with the above-described expression vector constitute another aspect of the present invention. As used herein, the term "transformation" means that DNA is introduced into a host so that DNA becomes replicable as an extrachromosomal factor or by completion of chromosomal integration. As used herein, the term "transfection" means that the expression vector is accepted by the host cell, whether or not any coding sequence is actually expressed.

The host cell of the present invention is a recombinant microorganism into which a vector having a polynucleotide encoding one or more target proteins is introduced, or a polynucleotide encoding one or more target proteins is introduced, and the polynucleotide is integrated into a chromosome to express the target protein. It may be a prokaryotic or eukaryotic cell. In addition, a host having a high DNA introduction efficiency and a high expression efficiency of the introduced DNA is usually used. Known eukaryotic and prokaryotic hosts such as E. coli, Pseudomonas, Bacillus, Streptomyces, fungi, yeast, insect cells such as Spodoptera frugiperda (SF9), animal cells such as CHO and mouse cells, African green monkey cells such as COS 1, COS 7, BSC 1, BSC 40 and BMT 10, and tissue cultured human cells are examples of host cells that can be used. In the case of using COS cells, since SV40 large T antigen is expressed in COS cells, the plasmid with the replication initiation point of SV40 is to exist as an episome of multiple copies in the cell. Higher than usual expression can be expected. The introduced DNA sequence may be obtained from the same species as the host cell, may be of a different species than the host cell, or it may be a hybrid DNA sequence comprising any heterologous or homologous DNA.

Of course, it should be understood that not all vectors and expression control sequences function equally in expressing the DNA sequence of the present invention. Likewise, not all hosts function equally for the same expression system. However, those skilled in the art can make an appropriate selection among various vectors, expression control sequences, and hosts without departing from the scope of the present invention without undue experimental burden. For example, when choosing a vector, you must consider the host, because the vector must be replicated within it. The number of copies of the vector, the ability to regulate the number of copies, and the expression of other proteins encoded by the vector, such as antibiotic markers, should also be considered. In selecting the expression control sequence, several factors must be considered. For example, the relative strength of the sequence, controllability, and compatibility with the DNA sequence of the present invention, etc., should be considered in particular with regard to possible secondary structures. Single-celled hosts should be selected, considering factors such as the selected vector, toxicity of the product encoded by the DNA sequence of the present invention, the secretion characteristics, the ability to accurately fold the protein, culture and fermentation requirements, the easiness in the purification of the product encoded by the present DNA sequence from the host. Within the range of these variables, one of ordinary skill in the art can select various vector/expression control sequence/host combinations capable of expressing the DNA sequence of the present invention in fermentation or large-scale animal culture. As a screening method for cloning the cDNA of the polypeptide of the present invention by expression cloning, a binding method, a panning method, a film emulsion method, or the like can be applied.

In the present invention, as a method of inserting the gene onto the chromosome of a host cell, a commonly known gene manipulation method can be used. The example of the non-viral delivery method includes a cell puncture method, lipofection, microinjection, ballistic method, virosome, liposome, Immunoliposomes, polyvalent cations or lipids: nucleic acid conjugates, naked DNA, artificial virons and chemical-promoting DNA influx. Sonoporation, for example, a method using the Sonitron 2000 system (RichMar) can also be used for the delivery of nucleic acids, and other representative nucleic acid delivery systems include the method such as Amaxa Biosystems (Cologne, Germany), Maxcyte, ATx (Rockville, Maryland) and BTX Molesular Syetem (Holliston, MA). The lipofection method is specified in U.S. Pat. Nos. 5,049,386, 4,946,787 and 4,897,355, and lipofection reagents are commercially available from for example, Transfectam™ and Lipofectin™. Cationic or neutral lipids suitable for effective receptor-recognition lipofection of polynucleotides include Feigner's lipids (WO91/17424 and WO91/16024) and can be delivered to cells through ex vivo introduction and into target tissues through in vivo introduction. Methods for preparing lipid:nucleic acid complexes including targeting liposomes such as immunolipid complexes are well known in the art (Crystal, Science., 270:404-410, 1995; Blaese et al., Cancer Gene Ther., 2:291-297, 1995; Behr et al., Bioconjugate Chem., 5:382389, 1994; Remy et al., Bioconjugate Chem., 5:647-654, 1994; Gao et al., Gene Therapy., 2:710-722, 1995; Ahmad et al., Cancer Res., 52:4817-4820, 1992; U.S. Pat. Nos. 4,186,183; 4,217,344; 4,235,871; 4,261,975; 4,485,054; 4,501,728; 4,774,085; 4,837,028; 4,946,787).

The affinity of the retrovirus can be changed by integration with the outer envelope protein, thus expanding the type of target cell. A lentiviral vector is a retroviral vector that transduces or infects non-dividing cells to produce high viral titers. The target tissue determines the retroviral gene delivery system. Retroviral vectors contain cis-acting long terminal repeats capable of packaging 6-10 kb external sequences. The minimal cis-acting LTR, sufficient for cloning and packaging of the vector, can be used to integrate therapeutic genes into target cells for permanent transgene expression. Widely used retroviral vectors include murine leukemia virus (MuLV), gibbon leukemia virus (GaLV), monkey immunodeficiency virus (SIV), human immunodeficiency virus (HIV), and combination viruses thereof (Buchscher et al., J. Virol., 66:2731-2739, 1992; Johann et al., J. Virol., 66:1635-1640 1992; Sommerfelt et al., Virol., 176:58-59, 1990; Wilson et al., J. Virol., 63:2374-2378, 1989; Miller et al., J. Virol., 65:2220-2224, 1991; PCT/US94/05700).

In the case of transient expression of sucrose phosphorylase, an adenovirus-based system is more widely used. An adenovirus-based vector causes highly efficient transduction in many cells, but does not require cell division. Using the vector, high titers and high levels of expression can be obtained, and can be mass-produced in a simple system. In addition, adeno-associated virus (AAV) vectors are used to transduce cells with target nucleic acids. For example, it is used for the production of nucleic acids and peptides in vitro and for gene therapy in vivo and ex vivo (West et al., Virology., 160:38-47, 1987; U.S. Pat. No. 4,797,368; WO93/24641, Kotin, Human Gene Therapy., 5:793-801, 1994; Muzyczka, J. Clin. Invest., 94:1351, 1994). The construction of a recombinant AAV vector is already known (U.S. Pat. No. 5,173,414; Tratschin et al., Mol. Cell. Biol., 5:3251-3260, 1985; Tratschin, et al., Mol. Cell. Biol., 4:20722081, 1984; Hermonat & Muzyczka, PNAS., 81:6466-6470, 1984; Samulski et al., J Virol., 63:038223828, 1989). In clinical trials, a gene transfer method using at least six viral vectors is used, which is an approach to complement the defective vector by inserting a gene into a helper cell line that produces a transducer. pLASN and MFG-S are examples of retroviruses used in clinical trials (Dunbar et al., Blood., 85:3048-305, 1995; Kohn et al., Nat. Med., 1:1017-102, 1995; Malech et al., PNAS., 94:(22)12133-12138, 1997). PA317/pLASN was the first therapeutic vector used for gene therapy (Blaese et al., Science., 270:475-480, 1995). The transduction efficiency of the MFG-S packaging vector was 50% or higher (Ellem et al., Immunol Immunother., 44(1):10-20, 1997; Dranoff et al., Hum. Gene Ther., 1:111-2, 1997).

Recombinant adeno-associated viral vectors (rAAV) are promising alternative gene delivery systems based on defective and non-pathogenic type 2 parvovirus adeno-associated viruses. All vectors are derived from plasmids with AAV 145 bp inverted terminal repeats flanking the transgene expression cassette. Efficient gene delivery and stable transgene delivery due to integration into the genome of the transduced cells are great advantages of this vector system (Wagner et al., Lancet., 351:9117-17023, 1998; Kearns et al., Gene Ther., 9:748-55, 1996).

In another aspect, the present invention provides a vaccine composition comprising
(1) a multi-epitope vaccine comprising an epitope represented by the amino acid sequence of SEQ ID NO: 1 and/or an epitope represented by the amino acid sequence of SEQ ID NO: 2; or
(2) a multi-epitope vaccine gene comprising a nucleic acid encoding an epitope represented by the amino acid sequence of SEQ ID NO: 1 and/or a nucleic acid encoding an epitope represented by the amino acid sequence of SEQ ID NO: 2; and
an adjuvant.

T-cells are directly involved in the role of detecting and mediating disease threats. Intercellular immunity regulated by T-cells (T lymphocytes) acts on B-cells to produce antibodies, and acts on macrophages to activate macrophages. In addition, it induces a cell-mediated immune response by acting on cytotoxic T cells (CTL).

The regulatory T cells (Treg cells), formerly known as suppressor T cells, are a subpopulation of T cells that modulate the immune system, maintain tolerance to self-antigens, and prevent autoimmune disease. Tregs are immunosuppressive and generally suppress or downregulate induction and proliferation of effector T cells.

The present inventors found that two epitopes (p485 and p527) elicit relatively much higher Th1 immunity coupled with lower Treg immunity.

In addition, in an embodiment of the present invention, it was confirmed that the vaccine composition induces a Th1 immune response through Th1 selection in PBMC (peripheral blood mononuclear cell).

A peripheral blood mononuclear cell (PBMC) is any peripheral blood cell having a round nucleus. These cells consist of lymphocytes (T cells, B cells, NK cells) and monocytes, whereas erythrocytes and platelets have no nuclei, and granulocytes (neutrophils, basophils, and eosinophils) have multi-lobed nuclei. In humans, lymphocytes make up the majority of the PBMC population, followed by monocytes, and only a small percentage of dendritic cells.

In the present invention, the term "Th1 cell" refers to a subset of helper T cell lymphocytes that are characterized in terms of gene expression, protein secretion and functional activity. For example, Th1 cells exhibit a cytokine expression pattern that synthesizes IL-2 and IFN-γ but not IL-4, IL-5, IL-10, and IL-13. Th1 cells are involved in cell-mediated immune responses to various intracellular pathogens, organ-specific autoimmune diseases, and delayed hypersensitivity reactions.

Interferon gamma (IFNγ), or type II interferon, is a cytokine that is critical for innate and adaptive immunity against viral, some bacterial and protozoal infections. IFNγ is an important activator of macrophages and inducer of Class II major histocompatibility complex (MHC) molecule expression.

The importance of IFNγ in the immune system stems in part from its ability to inhibit viral replication directly, and most importantly from its immunostimulatory and immunomodulatory effects. IFNγ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops.

The specific CTL and Th cell reactions and B-cell activation (serum-specific IgG and mucosal IgA antibodies) can be analyzed in BALB/c mice immunized with the multi-epitope vaccine. The multi-epitope-specific serum antibodies in patients with tumors can be analyzed using ELISA and western blotting. Thus, the multi-epitope vaccine could be considered as a diagnostic agent.

Figure 16:
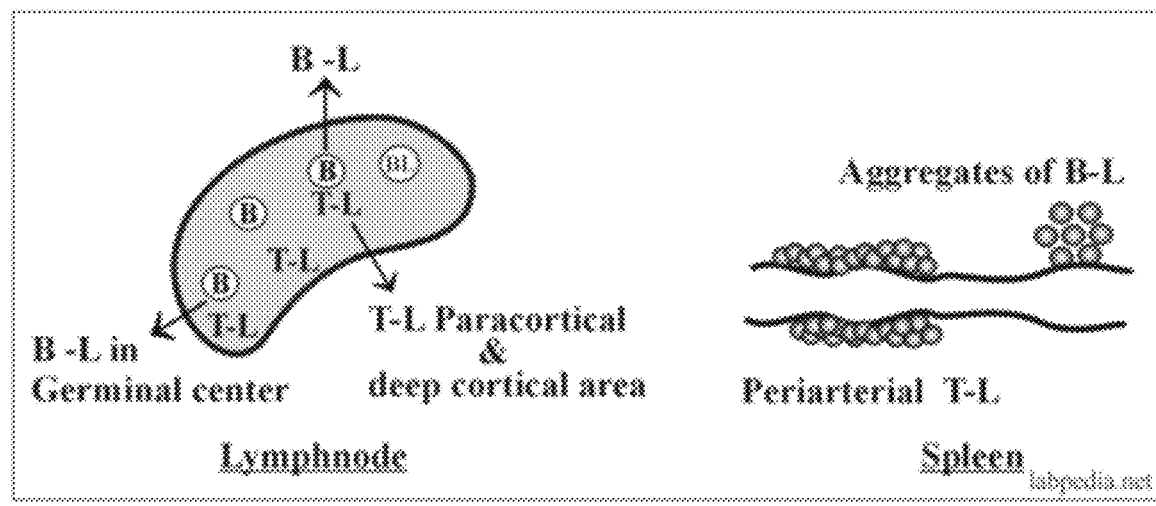
FIG. 16 is a conceptual diagram of a lymph node and spleen.

The spleen is an organ found in virtually all vertebrates. Similar in structure to a large lymph node, it acts primarily as a blood filter. The spleen plays important roles in regard to red blood cells (erythrocytes) and the immune system. The spleen synthesizes antibodies in its white pulp and removes antibody-coated bacteria and antibody-coated blood cells by way of blood and lymph node circulation. These monocytes, upon moving to injured tissue (such as the heart after myocardial infarction), turn into dendritic cells and macrophages while promoting tissue healing. The spleen is a center of activity of the mononuclear phagocyte system and is analogous to a large lymph node, as its absence causes a predisposition to certain infections (FIG. 16).

In addition to the epitope, the composition may further contain other ingredients for stabilizing the active ingredient.

According to an aspect of the present invention, concanavalin A (positive control) activates T cells, but does not activate B cells (when insolubilized, B cells are also activated). In addition, it is used as a means to study the specificity of the membrane structure of cancer cells because many cancer cells exhibit higher aggregation to Con A than normal cells.

When using the epitope peptide as a vaccine composition, it is preferable to use the active ingredient in a form mixed with a pharmaceutically acceptable carrier rather than used alone. Here, the pharmaceutically acceptable carrier includes carriers, excipients, and diluents commonly used in the pharmaceutical field.

Pharmaceutically acceptable carriers that can be used in the vaccine composition of the present invention are, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oils.

The vaccine composition of the present invention can be formulated and used in the form of oral dosage forms such as powders, granules, tablets, capsules, suspensions, emulsions, syrups, aerosols, etc., external preparations, suppositories, or sterile injectable solutions according to a conventional method. In the case of formulation, it may be prepared using diluents or excipients such as fillers, extenders, binders, wetting agents, disintegrants, and surfactants that are commonly used. Solid preparations for oral administration include tablets, pills, powders, granules, capsules, etc., and such solid preparations include active ingredients and at least one excipient, such as starch, calcium carbonate, sucrose, lactose, gelatin, etc. In addition to simple excipients, lubricants such as magnesium stearate and talc may also be used. Liquid preparations for oral use include suspensions, liquid solutions, emulsions, syrups, etc. In addition to commonly used diluents such as water and liquid paraffin, various excipients such as wetting agents, sweetening agents, fragrances, and preservatives may be included. Formulations for parenteral administration include sterile aqueous solutions, non-aqueous solutions, suspensions, emulsions, lyophilized formulations, and suppositories. Propylene glycol, polyethylene glycol, vegetable oils such as olive oil, injectable esters such as ethyloleate, and the like may be used as the non-aqueous solvent and suspension. As a base for suppositories, witepsol, tween 61, cacao butter, laurin paper, glycerogelatin, and the like may be used. In particular, in the case of a liquid formulation, it is preferable to sterilize by filtration through a bacteria trapping filter or the like or incorporation of a sterilizing agent. The sterilized composition can be solidified by, for example, lyophilization, and when used, it is dissolved in sterile water or a sterile diluent.

The vaccine composition according to the present invention can be administered to mammals such as cattle, rats, mice, livestock, dogs, humans, etc. by various routes. All modes of administration can be expected, for example, by oral, intravenous, intramuscular, subcutaneous, intraperitoneal injection.

In the present invention, the term "injection" or "administration" may vary depending on the age, sex, weight, etc. of the subject to be administered, and the dose of the vaccine may vary depending on the route of administration, the degree of disease, sex, weight, age, etc. have.

The dosage of the vaccine composition according to the present invention is selected in consideration of the animal's age, weight, sex, and physical condition. The amount required to induce an immunoprotective response in an animal without significant side effects may vary depending on the epitope used as an immunogen and any presence of excipients. In general, at each dose, the immunogenous amount of the polypeptide of the present invention contains 0.1 to 1000 μg of protein, preferably 0.1 to 100 μg, per ml of sterile solution. In the case of a vaccine composition, if necessary, the initial dose can be followed by optionally repeated antigen stimulation.

The vaccine composition of the present invention is applicable to early cancer.

Accordingly, in another aspect, the present invention provides a composition for preventing or treating cancer, comprising
(1) a multi-epitope vaccine comprising an epitope represented by the amino acid sequence of SEQ ID NO: 1 and/or an epitope represented by the amino acid sequence of SEQ ID NO: 2; or
(2) a multi-epitope vaccine gene comprising a nucleic acid encoding an epitope represented by the amino acid sequence of SEQ ID NO: 1 and/or a nucleic acid encoding an epitope represented by the amino acid sequence of SEQ ID NO: 2.

In the present invention, the cancer is at least one selected from the group consisting of for example, squamous cell cancer (e.g., epithelial squamous cell cancer), small cell lung cancer, non-small cell lung cancer, lung cancer, peritoneal cancer, colon cancer, biliary tract tumor, nasopharyngeal cancer, laryngeal cancer, bronchial cancer, oral cancer, osteosarcoma, gallbladder cancer, kidney cancer, leukemia, bladder cancer, melanoma, brain cancer, glioma, brain tumor, skin cancer, pancreatic cancer, breast cancer, liver cancer, bone marrow cancer, esophageal cancer, colon cancer, stomach cancer, cervical cancer, prostate cancer, ovarian cancer, head and neck cancer, and rectal cancer, but is not limited thereto.

In the present invention, the term "prevention" refers to any action of inhibiting or delaying the cancer by administration of the Hsp 90 epitope of the present invention, a transformant expressing the Hsp 90 epitope, or a composition comprising the Hsp 90 epitope or the transformant as an active ingredient.

In the present invention, the term "treatment" refers to any action in which the Hsp 90 epitope of the present invention, a transformant expressing the Hsp 90 epitope, or a composition comprising the Hsp 90 epitope or the transformant as an active ingredient is administered to stop division or benefit from the cancer or tumor without immortalization.

The term "therapeutically effective amount" used in combination with an active ingredient in the present invention refers to an amount effective for preventing or treating a target disease. The therapeutically effective amount of the composition of the present invention may vary depending on various factors, for example, the method of administration, the target site, and the condition of the patient. Therefore, when used in the human body, the dosage should be determined as an appropriate amount in consideration of safety and efficiency. It is also possible to estimate the amount used in humans from the effective amount determined through animal experiments.

In the present invention, the composition may further include an anticancer adjuvant.

In the present invention, the term "immune anticancer agent" is a therapeutic agent that induces immune cells to selectively attack only cancer cells by injecting artificial immune proteins into the body and stimulating the immune system, unlike existing anticancer drugs that attack cancer itself. It is an anticancer drug with a mechanism to restore or strengthen the immune system's ability to recognize or destroy tumors, to overcome the acquired immunosuppression or immune evasion mechanism in cancer cell. The immuno-anticancer agents include, but are not limited to, immune checkpoint inhibitors, immune cell therapy, and immunoviral therapy.

In the present invention, the term "immune checkpoint inhibitor" refer to a kind of immune modulating anticancer drug that supports activating CTL (cytotoxic lymphocytes), when some cancer cells evade bodily immune check point system. Examples thereof include, but are not limited to, a CTLA-4 inhibitor, a PD-1 inhibitor, a LAG-3 inhibitor, a TIM-3 inhibitor, a TIGIT inhibitor, and a VISTA inhibitor.

In an embodiment of the present invention, the immune anticancer agent may be an antagonist or modulator of an immune checkpoint molecule, for example any one selected from the group consisting of CTLA-4 (cytotoxic T-lymphocyte-associated protein 4), PD-1 (Programmed cell death protein 1), LAG-3 (Lymphocyte Activation Gene-3), TIM-3 (T-Cell Immunoglobulin and Mucin-domain containing-3), TIGIT (T-cell Immunoreptor with IG and ITIM domain), and VISTA (V-domain Ig Suppressor of T cell Activation). In en embodiment, the immune checkpoint antagonist or modulator may be a CTLA-4 inhibitor, but is not limited thereto. "CTLA-4 (cytotoxic T-lymphocyte-associated protein 4)" is also known as CD152 (Cluster of Differentiation 152) as an immunomodulatory inhibitor, and as a protein receptor acting as an immune checkpoint, it reduces the immune response.

In some embodiment of the present invention, the composition may further include an anti-cancer adjuvant.

According to an aspect, an "anti-cancer adjuvant" may be used to increase the anti-cancer effect of the anti-cancer agent, suppress or improve side effects of the anti-cancer agent, and may be administered to a patient in combination with an anti-cancer agent.

The anticancer adjuvant may be a STING (STimulator of InterferoN Gene) agonist, but is not limited thereto. In the present invention, the vaccine composition may additionally be administered in combination with an anticancer adjuvant, and the anticancer adjuvant may be a STING (STimulator of InterferoN Gene) agonist, but is not limited thereto.

In another aspect, the present invention relates to a method for treating or preventing cancer, comprising administering the vaccine composition to a cancer patient.

In one embodiment of the present invention, the vaccine composition may be characterized in that it is administered in combination with an immuno-anticancer agent, and it may be characterized in that it is administered in combination with an antibody therapeutic agent.

The immuno-anticancer agent or antibody therapeutic agent used in combination with the vaccine composition of the embodiments of the present invention may be administered simultaneously or sequentially with a time difference and may be selected according to an appropriate time and cycle.

According to an aspect of the present invention, the vaccine composition may be administered in combination with an anticancer agent. The immunological anticancer agents is an immune checkpoint inhibitor against any one selected from the group consisting of CTLA-4 (cytotoxic T-lymphocyte-associated protein 4), PD-1 (Programmed cell death protein 1), LAG-3 (Lymphocyte Activation Gene-3), TIM-3 (T-cell Immunoglobulin and Mucin-domain containing-3), TIGIT (T-cell Immunoreceptor with IG and ITIM domain), and VISTA (V-domain Ig Suppressor of T cell Activation), more preferably CTLA-4 inhibitors, but are not limited thereto.

In an aspect of the present invention, the vaccine composition may additionally be administered in combination with an anticancer adjuvant, and the anticancer adjuvant may be a STING (STimulator of InterferoN Gene) agonist, but is not limited thereto.

In another aspect, the present invention provides a multi-epitope vaccine-specific antibody, which is obtained from an animal inoculated with the multi-epitope vaccine of the present invention or the multi-epitope vaccine gene of the present invention. Further, the present invention provides a composition for preventing or treating cancer, comprising the multi-epitope vaccine-specific antibody of the fifth aspect of the present invention.

The multi-epitope vaccines of embodiments of the present invention can be considered as a promising strategy against tumors. The multi-epitope vaccine-specific antibodies perform anti-tumor tasks in target cells by antibody-dependent cell-mediated cytotoxicity (ADCC) and complement-dependent cytotoxicity (CDC).

In another aspect, the present invention provides an antibody (Ab) or antibody fragment that specifically binds to the epitope represented by the amino acid sequence of SEQ ID NO: 1 or the epitope represented by the amino acid sequence of SEQ ID NO: 2.

The antibody (Ab) or antibody fragment may target heat shock protein 90 and/or tumor cells.

Accordingly, the targeting antibody (Ab) or antibody fragment may be applied to antibody-drug conjugate (ADC) in which an antibody and a drug are combined, bispecific antibodies, and biobetters.

"Antibody" is used in the broadest sense, specifically encompass monoclonal antibodies, polyclonal antibodies, dimers, multimers, multispecific antibodies (eg, bispecific antibodies), and antibody fragments as long as they exhibit the desired biological activity (Miller et al. (2003) Jour. of Immunology 170:4854-4861).

"Antibody fragment(s)" comprises a portion of a full-length antibody, generally antigen binding or variable regions thereof. Examples of antibody fragments include Fab, Fab', F(ab')2, and Fv fragments; diabody; linear antibodies; minibody (Olafsen et al. (2004) Protein Eng. Design & Sel. 17(4):315-323), fragment produced by the Fab expression library, anti-idiotype (anti-Id) antibody, CDR (Complementarity determining regions), and epitope-binding fragments, single-chain antibody molecules of any of the above that immunospecifically bind to cancer cell antigens, viral antigens or microbial antigens; and multispecific antibodies formed from antibody fragments.

In the present invention, the term "antibody" is a substance produced by stimulation of an antigen in the immune system, also referred to as an immunoglobulin, and specifically binds to a specific antigen to float around the lymph and blood, causing an antigen-antibody reaction. While antibodies exhibit specificity for a specific antigen, immunoglobulins include both antibodies and antibody-like substances that lack antigen specificity. The latter polypeptide, for example, is produced at low levels in the lymphatic system and at increased levels by myeloma. In the present invention, it may be an antibody against an antigen prepared from a gene sequence comprising a sequence encoding a the Hsp 90 epitope, preferably an antibody against an antigen containing the amino acid sequence of SEQ ID NO: 1, the amino acid sequence of SEQ ID NO: 2, or the amino acid sequence of SEQ ID NO: 1 and SEQ ID NO: 2 in a fused form.

The epitope represented by the amino acid sequence of SEQ ID NO: 1 and/or the epitope represented by the amino acid sequence of SEQ ID NO: 2 can be used to detect immune cells and/or antibodies targeting tumor cells.

In addition, an aspect of the present invention uses the epitope represented by the amino acid sequence of SEQ ID NO: 1 and/or the epitope represented by the amino acid sequence of SEQ ID NO: 2 to boost and/or separate immune cells and/or antibodies targeting tumor cells from a biological sample.

The epitope represented by the amino acid sequence of SEQ ID NO: 1 and/or the epitope represented by the amino acid sequence of SEQ ID NO: 2 of the present invention can be used as a diagnostic agent.

Non-limiting examples of "biological sample" as used herein means any biological material from which nucleic acids and/or proteins can be obtained. As non-limiting examples, the term encompasses whole blood, peripheral blood, plasma, serum, saliva, mucus, urine, semen, lymph, fecal extract, cheek swab, cells or other bodily fluid or tissue, including but not limited to tissue obtained through surgical biopsy or surgical resection. Accordingly, an embodiment of the present invention provides composition or kit for monitoring immune response to an antigen of a tumor cell, comprising the epitope represented by the amino acid sequence of SEQ ID NO: 1 and/or the epitope represented by the amino acid sequence of SEQ ID NO: 2, or an antibody (Ab) or antibody fragment that binds to the epitope.

The epitope may bind to antibodies, B cells, and/or T cells, or the antibody (Ab) or antibody fragment may bind to tumor cells.

Further, the present invention provides a method for manufacturing an epitope or a peptide vaccine, comprising the step of:

designing an epitopes of heat shock protein 90 using a sequence selected from the group consisting of amino acid sequences of SEQ ID NOs: 1, 2, and 5 to 14; and synthesizing the epitope that binds to MHC class II using the amino acid sequence(s) selected in the previous step.

The amino acid sequences of SEQ ID NOs: 1, 2 and 5 to 14 can be used to design immunodominant epitopes of Hsp90.

The immune dominance of CD4 T cells is determined by the kinetic stability of an antigen protein (epitope). Antigen proteins exhibiting immune dominance showed very slow off-rates ($t_{1/2}$>75 h at pH 5.3), while other antigenic proteins separates more rapidly (t1/2<10 h). Therefore, if the amino acid that binds to MHC class II is changed so that it binds for a longer time, the immune dominance can be controlled, further increasing the efficiency in vaccine development.

Therefore, the epitope to be designed may be cancer immunodominant epitopes.

The synthesized epitope can be used to prepare an antibody (Ab) or antibody fragment targeting heat shock protein 90 or tumor cells. In addition, the synthesized epitope can be used to prepare a vaccine targeting tumor cells.

Further, an aspect of the present invention provides a method for manufacturing an epitope or a peptide vaccine, comprising the step of:

selecting the amino acid sequence of SEQ ID NO: 1 and/or the amino acid sequence of SEQ ID NO: 2; and using the amino acid sequence(s) selected in the previous step, to synthesize an epitope that boosts immune cells or induces antibodies targeting tumor cells or binds to immune cells or antibodies targeting tumor cells.

The epitope may bind to an antibody or may bind to a T cell receptor, a B cell receptor, and/or a major histocompatibility complex (MHC). The immune cells may be B cells or T cells.

The epitope could elicit either a cellular or a humoral immune response.

Further, the epitope could elicit CTL, Th and B cells and induce effective responses against a targeted tumor.

Hereinafter, the present invention will be described in more detail through examples. These examples are for illustrative purposes only, and it will be apparent to those of ordinary skill in the art that the scope of the present invention is not construed as being limited by these examples.

Materials and Methods

1. Patient Samples

Serum samples were obtained after written consent, from 25 HER2 positive breast cancer patient, and 25 volunteer donors at the Korea University Anam Hospital (Approval number: 2016AN0090). All sera were aliquoted and stored at −80° C. For human T cell response studies, peripheral blood mononuclear cells (PBMC) were obtained after informed consent, from 10 breast cancer patients, and 10 volunteer donors. Cells were ficolled and cryopreserved as previously described (Guy C T, et al. (1992) Expression of the neu protooncogene in the mammary epithelium of transgenic mice induces metastatic disease. *Proceedings of the National Academy of Sciences of the United States of America* 89(22):10578-10582). PBMC samples were obtained at the General Clinical Research Center Facility at the University of Washington (Approval number: NIH MO1-RR-00037)

2. Mice and Cell Line

Neu-transgenic mice [strain: FVB/N-Tg(MMTVneu) 202Mul] were obtained from the Jackson Laboratory (Bar Harbor, ME). These mice harbor non-mutated, non-activated rat neu under the control of the mouse mammary tumor virus (MMTV) promoter/enhancer. The neu transgene is expressed at low levels in normal mammary epithelium, salivary gland, and lung. Until the age of eight month, 35% of female neu-transgenic mice spontaneously develop mammary carcinomas that display high neu-expression levels. Mouse mammary carcinoma (MMC) cell line was established from a spontaneous tumor in neu-transgenic mouse. MMC cells were maintained in RPMI-1640 medium (ThermoFisher scientific, Utah, USA) supplemented with 10% fetal bovine serum, 100 units/ml penicillin, 100 mg/mL streptomycin and 2 mM L-glutamine, and were incubated in a humidified 37° C. incubator with 5% $CO_2$. Lapatinib was purchased from LC laboratories (L-4899, MA, USA). To generate lapatinib-resistant MMC cell line, MMC cells were cultured by twice weekly treated in the presence of increasing concentrations (100-300 nM) of lapatinib for 6 months. All cell lines were regularly tested for mycoplasma infection both before and after the study.

3. Scoring System for the Prediction of MHC Class II Binding Epitope

To identify HSP90-specific MHC class II epitopes that have optimal binding affinity and promiscuity across multiple alleles, a combined scoring system using widely available algorithms for predicting class II binding was utilized. Briefly, the following 5 algorithms were used for prediction of Class II peptides derived from the HSP90 peptide sequence: SYFPEITHI (Institute for Cell Biology, Heidelberg, Germany), Propred (Institute of Microbial Technology, Chandigarh, India), MHC-Thread (University of Aberdeen, Aberdeen, UK), Average Binding matrix method, and Rankpep (Havard, Boston, MA). Binding predictions were generated using each algorithm for the 15 most common MHC class II alleles: DRB1*0101, DRB1*1501, DRB1*0301, DRB1*0401, DRB1*0404, DRB1*0405, DRB1*0701, DRB1*0802, DRB1*0901, DRB1*1101, DRB1*1201, DRB1*1302, DRB3*0101, DRB4*0101, DRB5*0101. The 12 peptides described in this study were selected as follows. For each available MHC II allele from the five algorithms, 15 peptide sequences were initially selected solely based on the rank order of the predicted binding affinity. Individual amino acids for each selected peptide were assigned a score between 1 and 20, with 20 being an amino acid contained in a peptide sequence that ranked highest for predictive binding affinity across multiple algorithms. Top 12 HSP90 peptides were selected representing all potential “immunogenic hot spots”. Top 12 HSP90 peptides were synthesized from Anygen (Gwangju, Korea).

Table 1 below shows the selected Hsp 90 15-mer peptide sequences.

TABLE 1

| HSP90 15-mer peptide | amino acid sequences |
|---|---|
| p485-499 | LYVRRVFIMDNCEEL (SEQ ID NO. 1) |
| p527-541 | QSKILKVIRKNLVKK (SEQ ID NO. 2) |
| p109-123 | LYKDLQPFILLRLLM (SEQ ID NO. 5) |
| p145-159 | QAEIAQLMSLIINTF (SEQ ID NO. 6) |
| p160-174 | YSNKEIFLRELISNS (SEQ ID NO. 7) |
| p220-234 | MTKADLINNLGTIAK (SEQ ID NO. 8) |
| p255-269 | QFGVGFYSAYLVAEK (SEQ ID NO. 9) |
| p296-310 | TDTGEPMGRGTKVIL (SEQ ID NO. 10) |
| p328-342 | IVKKHSQFIGYPITL (SEQ ID NO. 11) |
| p457-471 | LEFRALLFVPRRAPF (SEQ ID NO. 12) |
| p582-596 | SELLRYYTSASGDEM (SEQ ID NO. 13) |
| p780-794 | SVKDLVILLYETALL (SEQ ID NO. 14) |

4. Animal Study

To test immunogenicity of the selected peptides in murine model, six to eight-week-old female FVB mice were obtained from Koatech (Gyeonggi, Korea). The mice were immunized subcutaneous (s.c) injection with 100 μg of respective HSP90 peptides of SEQ ID NOs: 1, 2, and 5-14 or Phosphate Buffered Saline (PBS) as a mixture in complete Freund's adjuvant (CFA; F5881, Sigma, MO, USA)/incomplete Freund's adjuvant (IFA; F5506, Sigma). Three immunizations were given 10 days apart. Ten days after the third vaccination, spleen and serum was harvested from each mouse.

For the tumorigenesis experiments of the selected peptides in murine model, six to eight-week-old female neu-transgenic mice were purchased from Jackson Laboratory. The mice were immunized s.c injection with 100 μg of each HSP90 peptides or PBS as a mixture in CFA/IFA. Three immunizations were given 10 days apart. Seven days after the third vaccination, MMC cells ($5 \times 10^5$) were transplanted with s.c in neu-transgenic mice. Three weeks after tumor implantation, spleen and tumor tissues were harvested from each mouse.

To evaluate effects of the combination therapeutic with HSP90 peptides and STING agonist (tlrl-dmx, InvivoGen, CA, USA), MMC cells ($5 \times 10^5$) were implanted with s.c in neu-transgenic mice. When the tumor reached a size greater than 100 mm$^3$, the mice were immunized subcutaneous injection with 100 μg of each HSP90 peptides or PBS as a mixture in CFA/IFA, and intraperitoneal (i.p) injection with STING agonist at 100 μg. Three immunizations were given 10 days apart. 15 days after the third vaccination, spleen, tumor and serum was harvested in mice. To evaluate survival analysis of the combination effects with HSP90 peptides and STING agonist, mice were monitored two time per week until 90 days following tumor implantation and when tumor reached a size greater than 2,000 mm$^3$, mice were considered dead.

To investigate effects of the combination therapeutic with HSP90 peptides/STING agonist/immune checkpoint inhibitor, MMC cells ($5 \times 10^5$) were injection with s.c in neu-transgenic mice. When the tumor reached a size greater than 100 mm$^3$, the mice were immunized s.c injection with 100 μg of each HSP90 peptides or PBS as a mixture in CFA/IFA, and treated i.p injection with STING agonist at 100 μg. After first immunization, anti-CTLA-4 mAb (BP0032, Bioxcell, NH, USA) as an immune checkpoint inhibitor was injected at 150 μg i.p twice a week until study end. Three immunizations were given 10 days apart. Two weeks after the third immunization, spleen, tumor and serum was harvested from mice.

To establishment lapatinib-resistant mouse model, MMC and lapatinib-resistant MMC cells (1×106) were injected flank with s.c in neu-transgenic mice. When the tumor reached a size greater than 100 mm$^3$, the mice were administrated by 5 times weekly to orally gavage with lapatinib (75 mg/kg) until the experimental end.

To investigate effects of the combination therapeutic with lapatinib/HSP90 peptides/STING agonist/immune checkpoint inhibitor, LR-MMC cells (1×106) were injection with s.c in neu-transgenic mice. When the tumor reached a size greater than 100 mm$^3$, the mice were immunized subcutaneous injection with 100 μg of each HSP90 peptides or PBS as a mixture in CFA/IFA, and treated i.p injection with STING agonist at 100 μg. After the first immunization, anti-CTLA-4 mAb (BP0032, Bioxcell, NH, USA) as an immune checkpoint inhibitor was injected i.p twice a week at 150 μg, and lapatinib was administrated 5 times weekly by oral gavage at 75 mg/kg until study end. Three immunizations were given 7 days apart. Two weeks after the third immunization, spleen, tumor and serum was harvested from mice. The tumor diameters of all experimental mouse were measured using calipers twice per week until the experimental end.

The tumor volumes were calculated using the following formula:

$$\text{Volume (mm}^3\text{)} = \text{width}^2 \times \text{length}/2.$$

All experimental procedures involving mice were performed with the guidance protocols approved by the Institutional Animal Care and Use Committee of Korea University (IACUC, Approval number: KOREA-2016-128). All method were carried out in accordance with the relevant guidelines and regulations.

5. HSP90 and HER2 ECD Enzyme-Linked Immunosorbent Assay (ELISA)

The levels of HSP90 and HER2 ECD were evaluated by ELISA in the serum of HER2 positive breast cancer patients and mice. Briefly, HSP90 (ADI-SPP-776, Enzo Life Science, NY, USA) and HER2 ECD (YCP5341, Speed Biosystems) recombinant proteins were coated a 96-well microplate with 50 μL per well of the diluted concentration of 20 μg/mL in carbonate buffer. Standard was coated with IgG dilution of human and mouse to serial concentration (0.64~0.005 μg/mL). After overnight incubation at 4° C. and were than blocked with 5% BSA in PBS-T for 1 hour at room temperature (RT). Samples (200 μL) were added to the wells and incubated overnight at 4° C. Subsequently, addition of working dilution (1:10,000) of anti-human (14506, Sigma) and anti-mouse (15381, Sigma) IgG-HRP for 45 minutes at RT and the reaction was visualized by the addition of 50 μL TMB solution (T0440, Sigma) for 5 minutes. The reaction was stopped with 50 μL stop solution ($H_2SO_4$). The optical density of each well at 450 nm was determined using an IMARKTM™ microplate reader (Bio-Rad Laboratories, Hercules, CA, USA).

6. Enzyme-Linked Immunosorbent Spot (ELISPOT) Assay

The frequency of interferon-gamma (IFN-γ) forming T cells was evaluated using ELISpot assay. Briefly, IP Sterile Clear 96-well plates (MAIPS4510, Merck Millipore, Darmstadt, Germany) were added 30 μL/well of 35% ethanol for 1 minute, and then washed with 200 μL PBS. Anti-mouse IFN-γ antibody (AN81, MabTech, Stockholm, Sweden) was coated IP Sterile Clear 96-well plate with 50 μL per well of the concentration of 10 μg/mL in PBS. After overnight incubation at 4° C. and were than blocked with 200 μL Mouse T cell media for 2 hour at 37° C. Splenocytes were plated at $2.5 \times 10^6$/mL, $3.5 \times 10^6$/mL with 10 μg/mL of HSP90 peptides, 10 μg/mL of tetanus toxoid (TT) peptide, 2.5 μg/mL of Concanavalin A, or medium alone in a total volume of 200 μL/well for 70-72 hours at 37° C. in 5% $CO_2$. The plates were washed with 200 μL of PBS in 0.05% Tween-20 (PBS-T). The wells were added with 50 μL diluted biotinylated anti-mouse IFN-γ antibody (R46A2, MabTech) (concentration of 5 μL/mL with PBS-T) for 16-24 hours at 4° C. After washing thrice with PBS, streptavidin-HRP (3310-9, MabTech) was diluted 1:250 and added at 50 μL/well for 1 hour at RT. After washing thrice with PBS, 50 μL/well of AEC Substrate Set (551951, BD Biosciences, CA, USA) development solution were added for up to 5-10 minute at RT. Color development was stopped by washing under tap water. After drying overnight in dark at RT, spots were counted using AID ISPOT™ reader system (AID, Strassberg, Germany).

7. Depletion of CD4+ or CD8+ T Cells In Vivo

Six to eight-week-old female neu-transgenic mice were purchased from Jackson Laboratory. Mice were i.p injected with 200 μg of anti-CD4 (BE0003-1, Bioxcell) or anti-CD8 (BE0061, Bioxcell) mAbs 3, 2 and 1 day before and then immunized. Three immunizations were given 10 days apart. After the first immunization, mAb against CD4 or CD8 were i.p injected with 200 μg twice a week until the end of experiment. Ten days after the third vaccination, MMC cells ($5\times10^5$) were implanted subcutaneously into neu-transgenic mice. Six weeks after tumor implantation, tumor tissue was harvested from mice. The tumor diameters were measured using calipers twice per week for more than six weeks. All experimental procedures involving mice were performed with the guidance protocols approved by the KUIACUC. All method were carried out in accordance with the relevant guidelines and regulations.

8. Cell Viability Assay

Cells were seeded at a density of $1\times10^5$ cells in 6-well plates. After 48 hours, the cells were treated with various concentrations of lapatinib. Cell viability was quantitatively analysed using the 3-[4,5-dimethylthiazol-2-yl]-2,5-diphenyltetrazolium (MTT) assay. Briefly, 100 μL of MTT (5 mg/mL in 1×PBS; M2128, Sigma) solution with 2 mL of complete media was added to the plate after treatment with lapatinib, and the plated further incubated for 3 hours at 37° C. The medium was removed. The plate to completely dry in the dark and 1 mL of dimethyl sulfoxide (DMSO; D8418, Sigma) was added to each well. Dissolved in 1 mL of DMSO and dispensed 100 μL into each well on a 96-well plate. The absorbance of the converted MTT dye was measured at 540 nm using an IMARK™ microplate reader (Bio-Rad Laboratories). Cell viability was expressed as the relative percentage compared to untreated cells; experimental error was also calculated. All experiments were repeated independently 3 times. The percent of cell survival was calculated using GRAPHPAD PRISM™ software version 5.01 (GraphPad Inc., La Jolla, CA, USA).

9. Western Blot Analysis

Tumors were harvested in PRO-PREP™ Protein Extraction Solution (17081, Intron, Gyeonggi, Korea) supplemented with XPERT™ phosphatase inhibitor cocktail solution (P3200, genDEPOT, TX, USA) and incubated on ice for 20 minutes. Protein concentrations were measured using Bio-Rad protein assay kits. Proteins (20 μg) were separated by electrophoresis on 8% SDS-polyacrylamide gels and transferred to BIOTRACE™ NT nitrocellulose membranes (66485, Pall Corporation, NY, USA). The membranes were blocked with 5% non-fat milk in Tris-buffered saline containing 0.1% Tween-20 (TBS-T) for 1 hour at RT and then incubated with the following primary antibodies overnight at 4° C.: p-HER2$^{Y1248}$ (#2247), HER3 (#12708), p-HER3$^{Y1289}$ (#2842), Met (3127), p-Met$^{Y1234/1235}$ (#3077), PI3K p85 (#4292), p-ERα (#2511), p-Akt$^{S473}$ (#9271) p-Erk (#9101) were obtained from Cell signaling technologies (MA, USA). HSP70 (sc-1060), p-HER2Y877 (sc-81505), p53 (sc-126), ERα (sc-8002) and p-EGFR (sc-57545) were obtained from Santa cruz biotechnology (TX, USA). HER2 p95 (#06-562) was obtained from Millipore Corp (MA, USA). HSP90 (#13171-1-AP) was obtained from Proteintech (IL, USA). p-PI3K$^{R1/R3\ Y458/Y199}$ (#PA5-17387) was obtained from Invitrogen (CA, USA). After washing 3 times in TBS-T, membranes were incubated for 1 hour at RT with anti-mouse or anti-rabbit horseradish peroxidase-conjugated secondary antibodies (170-6516, Bio-Rad Laboratories and sc-2004, Santa Cruz Biotechnology). Antibody-protein complexes were visualized using an ECL system (RPN2106, GE Healthcare, LC, UK) and SUPERSIGNAL™ West Femto Maximum Sensitivity Substrate (34095, Thermo Fisher Scientific, IL, USA), and the images were developed by CHEMIDOC™ Touch imaging system (Bio-Rad Laboratories).

10. Immunohistochemistry (IHC) Staining

Tumor tissues were fixed with 10% paraformaldehyde. Next, the tumors were stored in 70% ethanol and embedded in paraffin, sectioned and processed for staining with hematoxylin and Eosin (H&E). Paraffin-embedded tumor tissue slides were stained by IHC. Briefly, paraffin-embedded tumor specimens were deparaffinized in xylene (8587-4400, Dae Jung, Gyeonggi, Korea), rehydrated in a graded series of ethanol (100983, Merck Millipore), and washed in distilled water. Tumor tissue slides were blocked with 5% normal goat serum in 0.1% PBS-T between the primary antibodies and the tissue by incubate for 30-60 minutes at 37° C. The slides were incubated with CD8a monoclonal (14-0081-82, Thermo Fisher Scientific) primary purified antibody in 5% normal goat serum in 0.1% PBS-T for overnight at 4° C. Next day, after washing 4 times in 0.1% PBS-T, the slides were incubated with Goat anti-Rat IgG Alexa Fluor 594 conjugate (A-11006, Thermo Fisher Scientific) secondary antibodies in 5% normal goat serum in 0.1% PBS-T for 1 hour at RT in dark. After washing 3 times in 0.1% PBS-T, the slides were incubated with Alexa Fluor 488 anti-mouse CD4 (100423, Biolegend, CA, USA) second and secondary antibody in 5% normal goat serum in 0.1% PBS-T for 1 hour at RT in dark. After washing 3 times in 0.1% PBS-T, the slides were incubated with DAPI (4',6-diamidino-2-phenylindole dihydrochloride) (D9542, Sigma) in TE buffer (pH 8.0) for 15-20 minutes at RT in dark. After washing 3 times in 0.1% PBS-T, the slides were dried and mounted using Fluorescent mounting medium (S3023, Dako, CA, USA). IHC images were captured using an Olympus BX51 microscope (Olympus, Tokyo, Japan) equipped with DP70 digital camera and DP manager software. H&E images were captured using a Z1 Carl Zeiss microscope equipped with an AXIO scan (Zeiss, Gottingen, Germany). Optical density values were determined by AXIOSCAN Image processing software.

11. Statistics Analysis

All statistical analyses were performed using GRAPHPAD Prism software (version 5.01, San Diego, CA, USA). Differences between the two experimental groups was evaluated by Students t-test. Otherwise, differences between multiple experimental groups were examined by one-way and/or two-way analysis of variance (ANOVA) followed by the Tukey test. In all cases, a p-value of <0.05 was considered significant.

III. Results

1. HER2-Positive Breast Cancer Patients can have HSP90-Specific IgG Responses

To investigate the potential antibody immunity to HSP90 from HER2 positive breast cancer, an HSP90-specific antibody was evaluated in HER2 positive breast cancer patients and volunteer donors. The results of the ELISA assay showed that sera from HER2-positive breast cancer patients had HSP90-specific antibodies compared with the sera from the volunteer donors (mean median, 2.12 μg/mL vs. 0.08 μg/mL, p<0.0001). The levels of HSP90-specific antibody response were significantly higher in 25 HER2-positive breast cancer patients than in 25 volunteer donors (p<0.0001; FIG. 1).

Figure 3:
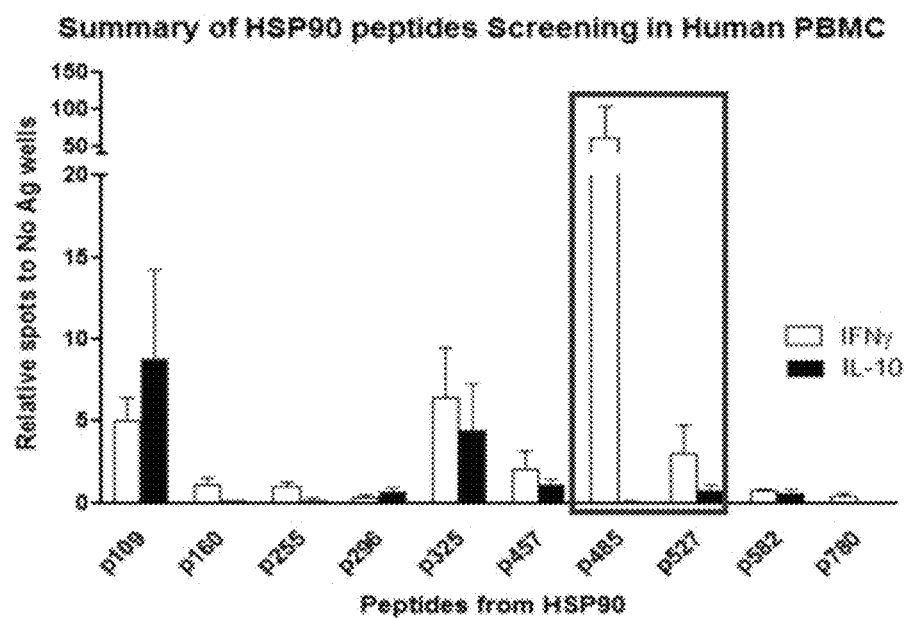

2. Selected Th1-Directed HSP90 Epitopes Elicit Strong Antigen-Specific T Cell Response in a Mouse Model This study profiled the peptide sequences with the highest recognition of HSP90 peptide and MHC class II peptide binding by a scoring system combining multiple MHC class II peptide binding algorithms. FIG. 2 depicts the entire HSP90 peptide sequence and identified immunogenic "hotspots". Among them, 11 peptides with the highest scores in the binding affinity scoring system were selected. The selected 11 15-mer HSP90 peptides (Table 2) were screened for T helper (Th)1 or Th2 immunity in human PBMCs from 10 volunteer donors by IFN-γ ELISPOT assay using as a representative Th1 cytokine, IFN-γ, and a Th2 cytokine, Interleukine-10 (IL-10). As shown in FIG. 3, Th1 and Th2 immune responses were found to have 3 patterns of responses by IFN-γ and IL-10 ELISPOT assays: strong Th1 and Th2 immune responses (p109 and p325 peptide), predominantly Th1 immune responses (p485 and p527 peptide), weak Th1 and Th2 immune responses (p160, p255, p296, p457, p582 and p780 peptide). Based on these results, p485 and p527 peptide were selected as promising Th1 epitopes with low potential for Th2 immunity induction.

Next, immunogenicity of each peptides in the murine model was evaluated. To confirm their immunogenicity, mice were immunized using 11 selected HSP90 peptides, and antigen-specific T cell responses were evaluated by IFN-γ ELISPOT assay. As shown in FIG. 4A, antigen-specific T cell response was significantly higher in peptide of p160, p457, p485 and p527 compared with control.

Based on human PBMC data, which showed a clear Th1 immunity, p485 and p527 peptides showed significantly higher antigen-specific T cell responses in a mouse model. Finally, two peptides (p485 and p527) were selected as candidate epitopes for the HSP90 vaccine. The immunogenicity of this two peptides mixture was further evaluated in a murine model. IFN-γ-ELISPOT responses were significantly higher to mixture of two peptides compared with the no antigen (No Ag) and tetanus toxoid (TT) peptide (FIG. 4B). These results indicated that HSP90 peptides was strongly produced immunogenicity in mouse model.

HSP90 sequence homology research was performed using the NCBI (National Center for Biotechnology Information, U.S. National Library of Medicine) system. The sequence of human HSP90 p485-499 (SEQ ID NO: 1) and p527-541 (SEQ ID NO: 2) were 100% identical with those of murine.

3. HSP90-Specific Immunity Inhibits Tumor Growth in Neu-Transgenic Mice

Figure 5A:
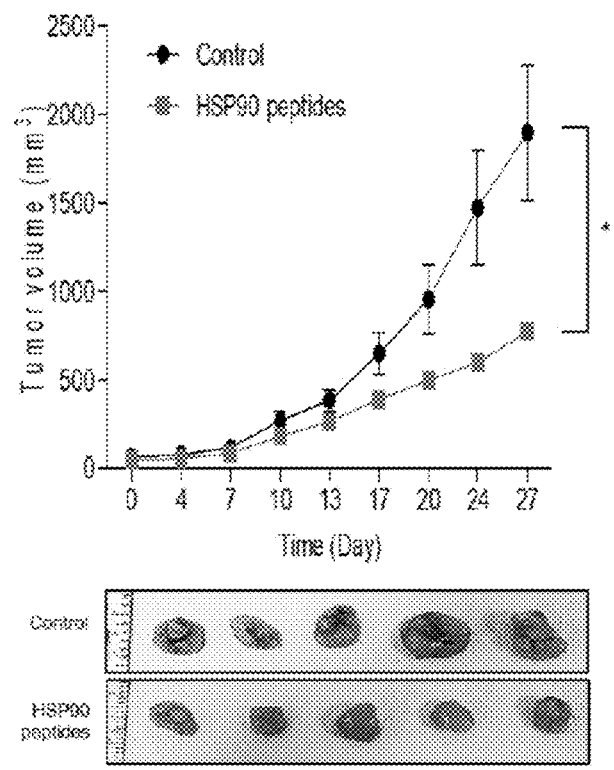
Figure 5B:
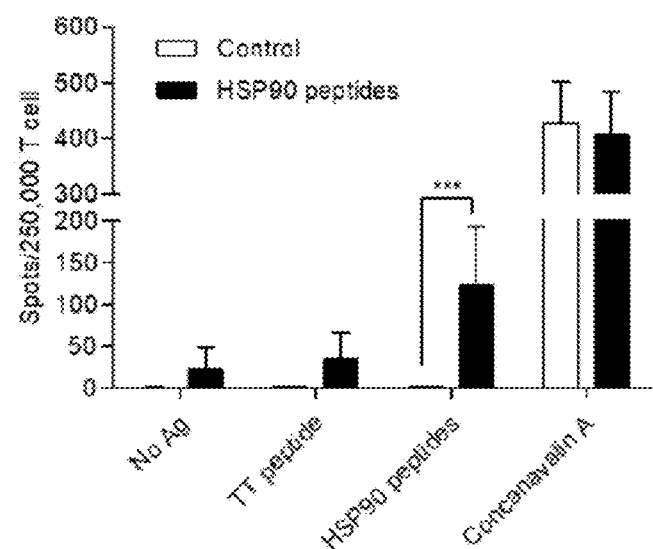
Figure 5C:
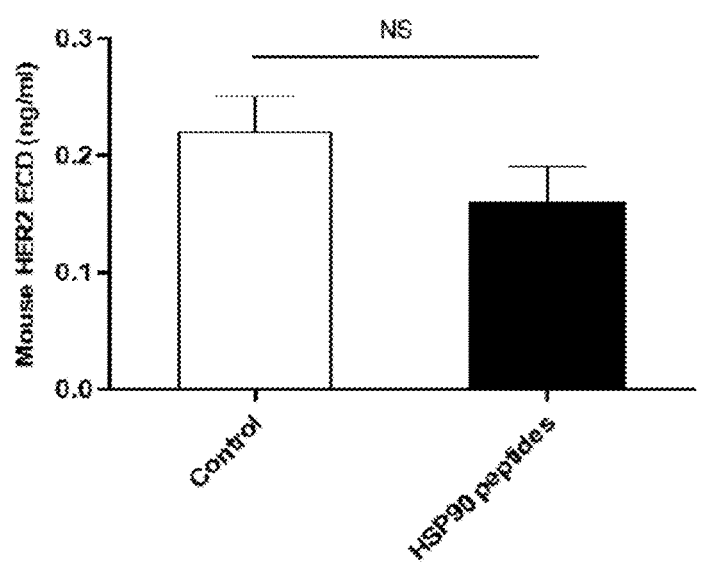
Figure 5D:
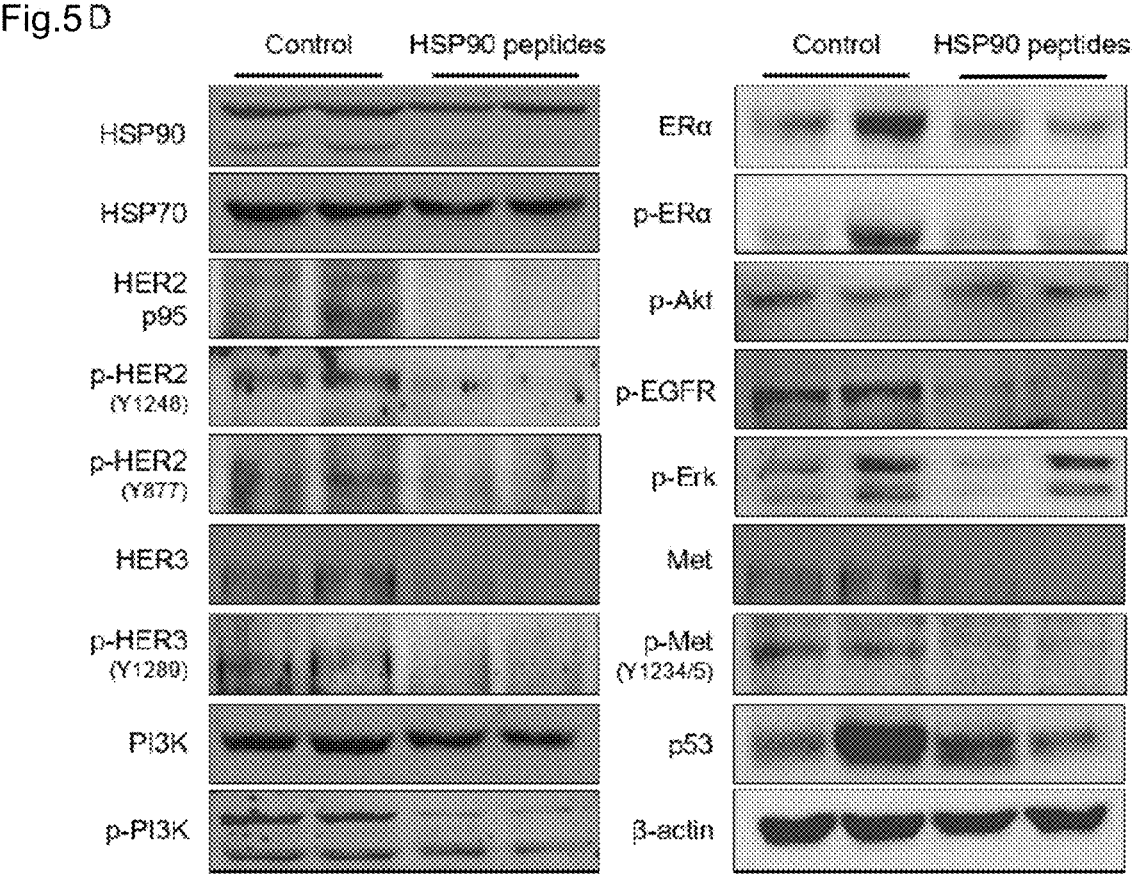

The next question was whether immunity to HSP90 can affect tumor growth in vivo. For the animal study, mouse mammary carcinoma (MMC) cells established from a spontaneous tumor in the neu-transgenic mice were used. As shown in FIG. 5A, 3 times of HSP90 peptide vaccination (mean±SD; 774±43 mm$^3$) significantly inhibited the tumor growth compared with control group (mean±SD; 1896±383 mm$^3$; p<0.05). The IFN-γ ELISPOT assay showed that HSP90 peptide vaccination significantly increased HSP90-specific IFN-γ-secreting T cells compared to that in the control (FIG. 5B). Next, to measure the changes in the expression levels of HER2 extracellular domain (ECD) in serum of mice as a biomarker of breast cancer after vaccination of HSP90 peptides, ELISA was conducted using sera of experimental mice. The expression levels of mouse HER2 ECD was significantly decreased in the HSP90 peptide vaccine group compared with that in the control group at the time of sacrifice (mean median, 0.22 ng/mL vs 0.16 ng/mL, p=NS, FIG. 5C). In addition, to investigate the correlation between changes in the serum levels of HER2 ECD and HER2 status of the tumor after vaccination with HSP90 peptides, the expression levels of HER2-related proteins were assessed by western blot analysis of the protein extracts from tumors of each experimental mouse. As shown in FIG. 5D, the expression levels of HSP90, HSP70, HER2 p95, p-HER2, p-PI3K, and p-EGFR decreased in HSP90 peptides groups compared with that in the control groups; however, the expression levels of p-Akt were not altered in HSP90 peptides groups.

Altogether, these results indicate that immunization with peptides derived from HSP90 affects the in vivo tumor growth through induction of HSP90-specific T cells response and changes in expression of HSP90 client proteins.

TABLE 2

Sequences and homology of peptides derived from HSP90

| HSP90 peptides | Sequences | | % Homology with mouse HSP90 |
|---|---|---|---|
| p109-123 | LYKDLQPFILLRLLM | (SEQ ID NO: 5) | 50 |
| p145-159 | QAEIAQLMSLIINTF | (SEQ ID NO: 6) | 100 |
| p160-174 | YSNKEIFLRELISNS | (SEQ ID NO: 7) | 100 |
| p220-234 | MTKADLINNLGTIAK | (SEQ ID NO: 8) | 100 |
| p255-269 | QFGVGFYSAYLVAEK | (SEQ ID NO: 9) | 100 |
| p296-310 | TDTEPMGRGTKVILL | (SEQ ID NO: 10) | 100 |
| p328-342 | IVKKHSQFIGYPITL | (SEQ ID NO: 11) | 100 |
| p457-471 | LEFRALLFVPRRAPF | (SEQ ID NO: 12) | 100 |
| p485-499 | LYVRRVFIMDNCEEL | (SEQ ID NO: 1) | 100 |
| p527-541 | QSKILKVIRKNLVKK | (SEQ ID NO: 2) | 100 |
| p582-596 | SELLRYYTSASGDEM | (SEQ ID NO: 13) | 100 |
| p780-794 | SVKDLVILLYETALL | (SEQ ID NO: 14) | 100 |

4. Efficiency of HSP90 Peptides on T Lymphocyte Depletion In Vivo

To investigate the relationship between the roles of $CD4^+$ or $CD8^+$ T cell responses and HSP90 peptide immunization, depletion of $CD4^+$ or $CD8^+$ T cells was performed using i.p injections of mAbs for 3 consecutive days before HSP90 peptide immunization in neu-transgenic mice. As shown in FIG. 6A, antibody-mediated CD4 and CD8 depletion rapidly accelerated the tumor growth after HSP90 peptide immunization. Antibody-mediated CD4 depletion accelerated the tumor growth compared with depletion of anti-CD8 after HSP90 peptide immunization. In addition, antibody-mediated CD8 depletion did not decrease tumor growth compared to control. However, only the HSP90 peptide immunization group showed inhibited tumor growth compared with control group. These results indicated that both $CD4^+$ and $CD8^+$ T cells play a role in anti-tumor response after HSP90 peptides immunization. The distribution of $CD4^+$ and $CD8^+$ T cells was evaluated by immunohistochemical staining. As shown in FIG. 6B, $CD4^+$ and $CD8^+$ T cells were abundantly distributed in the tumor of only the HSP90 peptide immunization group. Tumors of the $CD4^+$ or $CD8^+$ T cells depletion groups showed a low distribution of $CD4^+$ or $CD8^+$ T cells in the presence of HSP90 peptide immunization, and CD4 depletion was not sufficient to cause tumor suppression compared with CD8 depletion. In addition, both the depletion of CD4 and CD8 decreased distribution of $CD4^+$ and $CD8^+$ T cells. Taken together, the results demonstrated a mutual dependence of $CD4^+$ and $CD8^+$ T cell responses as a precondition for efficient tumor suppression by immunization using HSP90 epitopes.

5. Combination Effect with HSP90 Peptides and STING Agonist Induces HSP90-Specific Immunity and Inhibits Tumor Growth in Neu-Transgenic Mice Recent evidence has indicated that STING is involved in generation of spontaneous anti-tumor T cell responses important for the main innate immune pathway. Based on these findings, STING agonists have been studied as cancer therapeutics. The next question in this study was whether activation of innate immunity by a STING agonist is synergistic with HSP90 peptides. To confirm this hypothesis, the STING agonist was examined as a combination therapy with HSP90 peptide vaccine in neu-transgenic mice. When the implanted tumors in each experimental mice reached 100 $mm^3$, mice were treated 3 times with STING agonist and/or HSP90 peptides. The mean tumor volumes in each group of mice on day 35 showed a clear difference according to treatment. Tumors of control group (mean±SD; 1754±245 $mm^3$) showed the most rapid growth, followed by the tumors of HSP90 peptides immunization group (mean±SD; 895±196 $mm^3$), tumors of STING agonist treatment group (mean±SD; 647±66 $mm^3$), and then tumors of the combination treatment with HSP90 peptides and STING agonist (mean±SD; 478±112 $mm^3$) group. Notably, the STING agonist alone (mean±SD; 647±66 mm3) had similar tumor growth compared with HSP90 peptides immunization, and the best anti-tumor effects was obviously obtained by combination of HSP90 peptides and STING agonist (mean±SD; 478±112 $mm^3$; FIG. 7A). The expression levels of mouse HER2 ECD was significantly diminished in the HSP90 peptides (300 µg/mL) or STING agonist (89 µg/mL) group compared with the control (603 µg/mL), as assessed by ELISA. Especially, the combination of HSP90 peptides and STING agonist (49 µg/mL) completely decreased the level of HER2 ECD compared with control and HSP90 peptides group (FIG. 7B). The tumor-inhibitory effect was associated with the HSP90-specific IFN-γ-secreting T cell responses in HSP90 peptides immunization. Therefore, HSP90-specific IFN-γ-secreting T cell responses were statistically significantly enhanced in the combination treatment with HSP90 peptides and STING agonist (FIGS. 7C-7F).

Figure 8:
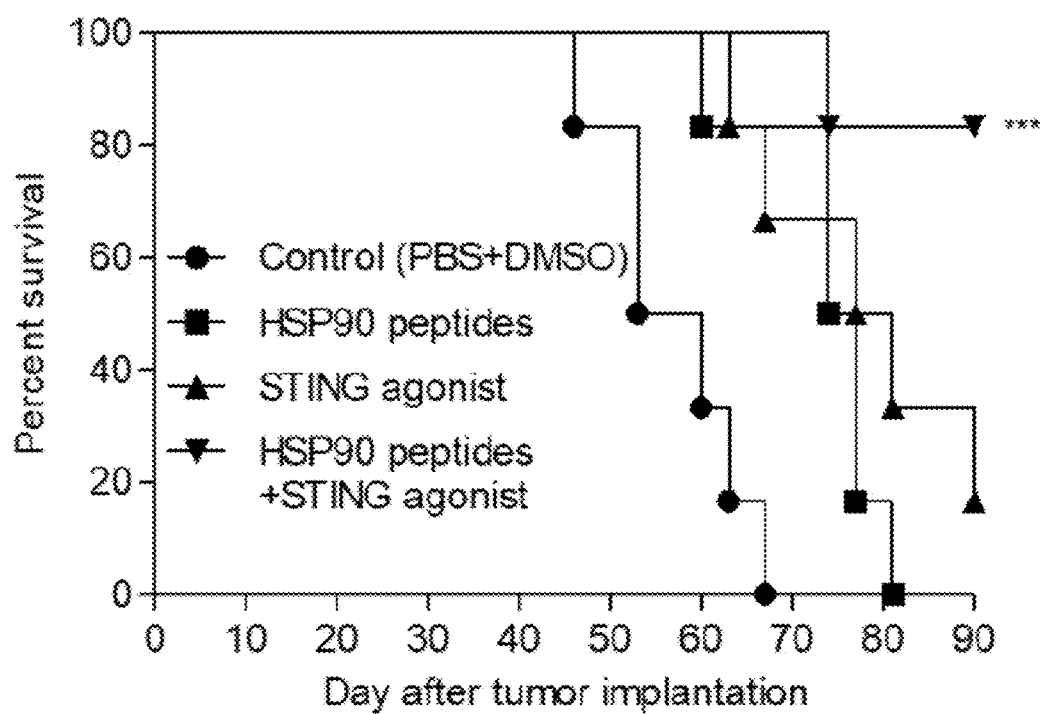

6. Combination Therapy with HSP90 Peptides and STING Agonist Improves Survival in Neu-Transgenic Mice Next, this study evaluated whether STING agonist treatment could augment the anti-tumor activity of HSP90 peptides and result in the survival of tumor-bearing neu-transgenic mouse model. Immunization with HSP90 peptides was conducted on days 10, 17 and 24 after tumor implantation. Although both HSP90 peptides immunization (median survival: 75.5 days) and STING agonist alone (median survival: 79 days) improved the survival of mice compared with that in the control (median survival: 56.5 days), the combination with HSP90 peptides and STING agonist (median survival: 90 days; p<0.001) significantly extended the median survival period (FIG. 8). These results suggest that the combination of STING agonist with HSP90 peptides led to a longer survival in mice by enhancing the HSP90-specific T cell immunity, resulting better anti-tumor activity in vivo.

7. Combination Therapeutic with HSP90 Peptides/STING Agonist/Anti-CTLA-4 Ab Inhibits Tumor Growth and Enhances HSP90-Specific Immunity in Neu-Transgenic Mice Although development of anti-HER2 therapeutics has revolutionized the prognosis of patients with HER2 type cancers, resistance to anti-HER2 therapeutics eventually occurs in metastatic context. Thus, the final aim of this study was to develop an HSP90 peptide vaccine for therapeutic purpose. To this end, HSP90 peptides were evaluated in combination with the STING agonist and anti-CTLA-4 Ab in neu-transgenic mouse model. As shown in FIG. 9A, the combination of HSP90 peptides and anti-CTLA-4 Ab was significantly more effective in suppressing tumor growth compared with the control or HSP90 peptides only. The best anti-tumor effect was observed in the group that received triple combination therapy with HSP90 peptides/STING agonist/anti-CTLA-4 Ab. The expression levels of mouse HER2 ECD diminished in all experimental groups compared with control group, however, there was no difference among the experimental groups (FIG. 9B). As expected, significant HSP90-specific T cell responses were observed in the HSP90 peptides immunized groups only (FIG. 9C-9G). Although the combination of STING agonist and anti-CTLA4 Ab showed a good anti-tumor effect, HSP90-specific T cell response was not observed.

Additionally, to investigate the biological changes induced by each treatment in the tumors, the expression levels of HER2-related proteins in the implanted tumors were evaluated by western blot analysis. The expression levels of HER2-related proteins were found to be decreased by the triple combination of HSP90 peptides/STING agonist/anti-CTLA-4 Ab compared with that in the other groups. To further investigate on the tumor microenvironment, the distribution of T cells was assessed by IHC staining in the tumor tissues. FIGS. 10A-10C. The number of infiltrated $CD4^+$ and $CD8^+$ T cell in tumor was increased the most by the triple combination therapy with HSP90 peptides/STING agonist/anti-CTLA-4 Ab. Of note, the combination of anti-CTLA-4 Ab and HSP90 peptides did not increase $CD8^+$ T cells compared with HSP90 peptides only (Mean median; 9 vs. 12.5 counts, p=NS). However, the STING agonist clearly induce more infiltration of $CD8^+$ T cells compared with the tumors from the combination of HSP90 peptides and anti-CTLA4 Ab (Mean median; 78.6 vs. 12.5 counts, p<0.001). Taken together, these results suggest that the combination therapy with STING agonist and an immune checkpoint inhibitor enhanced the anti-tumor activity of the HSP90 peptides by potentiating HSP90-specific T cell responses.

8. Establishment of Lapatinib-Resistant Mouse Mammary Carcinoma Cells and Mouse Model To study efficacy of HSP90 peptides vaccine in lapatinib-resistant cancer, MMC cells were exposed to lapatinib in vitro to establish mouse model of acquired resistance. As shown in FIG. 11A, the cell viability of both the parent and lapatinib-resistant cells was evaluated after treatment with increasing doses of lapatinib, and $IC_{50}$ values were determined by MTT assay. The $IC_{50}$ value after lapatinib treatment increased in LR-MMC cells (390 nM) compared to parent MMC cells (76 nM). In LR-MMC cells, lapatinib did not induce significant apoptosis compared with the MMC cells. In contrast, MMC cells were sensitive in a dose-dependent manner after lapatinib treatment. The lapatinib-resistant mouse model was evaluated by examining the effect of lapatinib treatment on tumor growth after implanting LR-MMC cells in neu-transgenic mice (FIG. 11B). In the MMC tumor-bearing experimental group mice, lapatinib significantly inhibited tumor growth on day 34; the mean tumor volume of the lapatinib-treated and control group were 1711±397 mm³ and 389±106 mm³, respectively (mean±SD, p<0.05). In the experimental groups with LR-MMC tumor bearing mice, the mean tumor volume in lapatinib-treated group was smaller than that in the control group; lapatinib-treated group versus control group was 1212±523 mm³ and 609±517 mm³, but it was not statistically significant (mean±SD, p=NS).

9. HSP90 Inhibitor (17-DMAG) Enhances Combination Effect with Lapatinib in Lapatinib-Resistant Mouse Mammary Carcinoma Cells In Vitro To investigate the potential effects of 17-DMAG in the presence of acquired resistance to lapatinib in vitro, changes in the expression of HER2-related proteins were evaluated by western blot analysis. As shown in FIG. 12A, the expression levels of almost all HER2-related proteins were significantly increased in the LR-MMC cells compared with the MMC cells. In addition, the expression levels of p-HER2, p-EGFR, p-Akt, and p-Erk decreased following the combination treatment with 17-DMAG and lapatinib in both the MMC and LR-MMC cells (FIG. 12B). These results suggest that HSP90 inhibitor plays a significant role in the cancer cell biology of HER2-positive breast cancer with acquired resistance to lapatinib.

10. Combination Therapeutic with Lapatinib/HSP90 Peptides/STING Agonist/Anti-CTLA-4 Ab Inhibits Tumor Growth and Enhances HSP90-Specific Immunity in Lapatinib-Resistant Mouse Model The findings of in the in vitro studies were further evaluated in mouse model. The aim of the next experiment was to demonstrate whether the combination of lapatinib/HSP90 peptides/STING agonist/anti-CTLA-4 Ab is effective in overcoming the acquired resistance to lapatinib in vivo. As shown in FIG. 13A, the combination effect of lapatinib/HSP90 peptides/anti-CTLA-4 Ab significantly inhibited the tumor growth compared with the control and the combination treatment of lapatinib and HSP90 peptides. In addition, the best anti-tumor response was observed in response to the combination treatment with lapatinib/HSP90 peptides/STING agonist/anti-CTLA-4 Ab group (p<0.001). In particular, the HSP90-specific IFN-γ-secreting T cell response was significantly enhanced in response to the combination treatment of lapatinib/HSP90 peptides/STING agonist/anti-CTLA-4 Ab (FIGS. 13B-13F). These results suggested that improved anti-tumor efficacy was intimately associated with increased HSP90-specific T cell responses, as evaluated by the IFN-γ ELISPOT assay. Furthermore, to investigate the effects on immune microenvironment, T cell distribution was evaluated by IHC staining using tumors from each experimental mice. As shown in FIG. 14, the number of infiltrated $CD4^+$ and $CD8^+$ T cell in the tumor was most increased in the combination therapy with lapatinib/HSP90 peptides/STING agonist/anti-CTLA-4 Ab group (Mean median; 87.8 counts). The combination of HSP90 peptides and lapatinib further increased the number of infiltrated CD8+ T cells compared with the lapatinib only (Mean median; 26.9 vs. 6.6 counts). In addition, the STING agonist clearly induce more infiltration of $CD8^+$ T cells compared with the tumors from the combination treatment of lapatinib/HSP90 peptides/anti-CTLA4 Ab (Mean median; 78.6 vs. 54.6 counts).

Figure 13H:
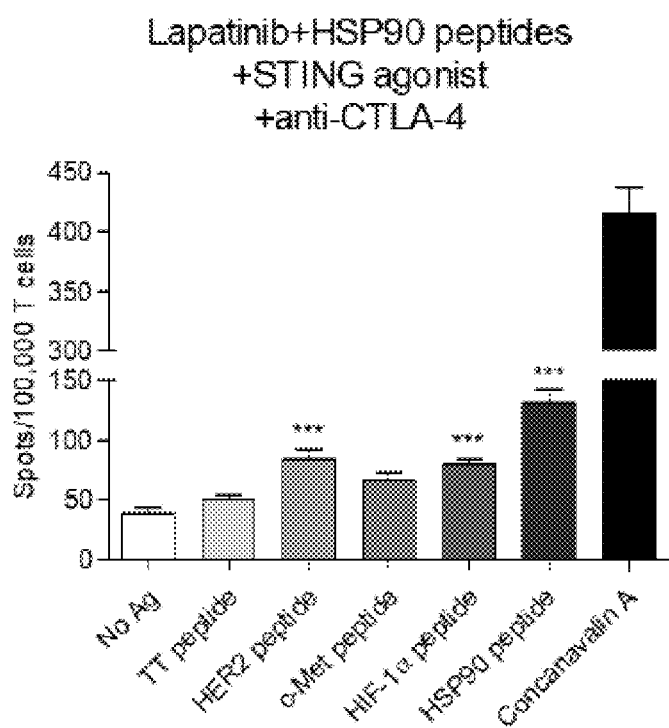

To investigate the potential epitope-spreading of other peptides, IFN-γ ELISPOT assay was conducted using peptides from HER2, c-MET and HIF-1α. As shown in FIGS. 13G and H, additional antigen-specific T cell responses to HER2, HIF-1α were induced in the combination treatment of lapatinib/HSP90 peptides/STING agonist/anti-CTLA-4 Ab group (p<0.001; FIG. 13H). However, epitope-spreading was not observed in the combination treatment of lapatinib/HSP90 peptides/anti-CTLA-4 Ab group (FIG. 13G). Taken together, these results demonstrate that HSP90 peptides in combination with STING agonist and an immune checkpoint inhibitor is a promising immunologic strategy in lapatinib-resistant HER2 positive advanced breast cancer.

As described above, specific parts of the present invention have been described in detail, and it will be apparent to those of ordinary skill in the art that these specific techniques are only preferred embodiments, and the scope of the present invention is not limited thereby. Therefore, it will be said that the practical scope of the present invention is defined by the appended claims and their equivalents.

The invention claimed is:

1. A method for treating cancer in a subject in need thereof, comprising administering to the subject an effective amount of a composition, wherein the composition comprises a mixture of two different MHC class II-specific epitopes from a heat shock protein 90 (HSP90), wherein the two MHC class II-specific epitopes consist of the amino acid sequence of SEQ ID NO: 1 and the amino acid sequence of SEQ ID NO: 2, wherein the composition further comprises an anticancer adjuvant.

2. The method for treating cancer according to claim 1, wherein the composition induces production of an antibody and/or activation of immune cells that recognizes heat shock protein 90 as an antigen.

3. The method for treating cancer according to claim 1, wherein the composition further comprises STING (Stimulator of Interferon gene) agonist.

4. The method for treating cancer according to claim 1, wherein the composition further comprises an immune checkpoint inhibitor against any one selected from the group consisting of CTLA-4 (cytotoxic T-lymphocyte-associated protein 4), PD-1 (Programmed cell death protein 1), LAG-3 (Lymphocyte Activation Gene-3), TIM-3 (T-cell Immunoglobulin and Mucin-domain containing-3), TIGIT (T-cell Immunoreceptor with IG and ITIM domain), and VISTA (V-domain Ig Suppressor of T cell Activation).

5. The method for treating cancer according to claim 1, wherein the cancer is selected from the group consisting of squamous cell cancer, small cell lung cancer, non-small cell lung cancer, lung cancer, peritoneal cancer, colon cancer, biliary tract tumor, nasopharyngeal cancer, laryngeal cancer, bronchial cancer, oral cancer, osteosarcoma, gallbladder cancer, kidney cancer, leukemia, bladder cancer, melanoma, brain cancer, glioma, brain tumor, skin cancer, pancreatic cancer, breast cancer, liver cancer, bone marrow cancer, esophageal cancer, colon cancer, stomach cancer, cervical cancer, prostate cancer, ovarian cancer, head and neck cancer, rectal cancer, and a combination thereof.

6. A method for treating cancer in a subject in need thereof, comprising administering to the subject an effective amount of a composition, wherein the composition comprise nucleic acid molecules encoding the two MHC class II-specific epitopes, as described in claim 1, wherein the composition further comprises an anticancer adjuvant.

7. A method for treating cancer in a subject in need thereof, comprising administering to the subject an effective amount of a composition, wherein the composition comprises an isolated heat shock protein 90 (HSP90)-specific MHC class II epitope, wherein the epitope consists of a peptide selected from the group consisting of SEQ ID NOs: 1, 2, 5, 6, 7, 8, 9, 10, 11, 12, 13, and 14, wherein the composition further comprises an anticancer adjuvant.

8. The method for treating cancer according to claim 7, wherein the composition induces production of an antibody and/or activation of immune cells that recognizes heat shock protein 90 as an antigen.

9. The method for treating cancer according to claim 7, wherein the composition further comprises an anticancer adjuvant.

10. The method for treating cancer according to claim 7, wherein the composition further comprises STING (Stimulator of Interferon gene) agonist.

11. The method for treating cancer according to claim 7, wherein the composition further comprises an immune checkpoint inhibitor against any one selected from the group consisting of CTLA-4 (cytotoxic T-lymphocyte-associated protein 4), PD-1 (Programmed cell death protein 1), LAG-3 (Lymphocyte Activation Gene-3), TIM-3 (T-cell Immunoglobulin and Mucin-domain containing-3), TIGIT (T-cell Immunoreceptor with IG and ITIM domain), and VISTA (V-domain Ig Suppressor of T cell Activation).

12. The method for treating cancer according to claim 7, wherein the cancer is selected from the group consisting of squamous cell cancer, small cell lung cancer, non-small cell lung cancer, lung cancer, peritoneal cancer, colon cancer, biliary tract tumor, nasopharyngeal cancer, laryngeal cancer, bronchial cancer, oral cancer, osteosarcoma, gallbladder cancer, kidney cancer, leukemia, bladder cancer, melanoma, brain cancer, glioma, brain tumor, skin cancer, pancreatic cancer, breast cancer, liver cancer, bone marrow cancer, esophageal cancer, colon cancer, stomach cancer, cervical cancer, prostate cancer, ovarian cancer, head and neck cancer, rectal cancer, and a combination thereof.

13. A method for treating cancer in a subject in need thereof, comprising administering to the subject an effective amount of a composition, wherein the composition comprises nucleic acid molecule encoding an epitope consisting of a peptide selected from the group consisting of SEQ ID NOs: 1, 2, 5, 6, 7, 8, 9, 10, 11, 12, 13, and 14, wherein the composition further comprises an anticancer adjuvant.

* * * * *